US012674807B2

(12) United States Patent
Mallick et al.

(10) Patent No.: US 12,674,807 B2
(45) Date of Patent: Jul. 7, 2026

(54) SYSTEMS, METHODS AND COMPOSITIONS FOR ANALYSIS OF PROTEOFORMS

(71) Applicant: Nautilus Subsidiary, Inc., Seattle, WA (US)

(72) Inventors: Parag Mallick, San Mateo, CA (US); Jarrett D. Egertson, Rancho Palos Verdes, CA (US); Gregory Kapp, San Carlos, CA (US); Kara Juneau, San Carlos, CA (US); Vivekananda Budamagunta, San Carlos, CA (US); Sanjib Guha, Redwood City, CA (US); James Henry Joly, San Francisco, CA (US); Steven Tan, San Mateo, CA (US); Zhengjian Zhang, Albany, CA (US); Maryam Jouzi, Hayward, CA (US)

(73) Assignee: NAUTILUS SUBSIDIARY, INC., Seattle, WA (US)

( * ) Notice: Subject to any disclaimer, the term of this patent is extended or adjusted under 35 U.S.C. 154(b) by 0 days.

(21) Appl. No.: 19/279,954

(22) Filed: Jul. 24, 2025

(65) Prior Publication Data

US 2026/0029416 A1     Jan. 29, 2026

Related U.S. Application Data

(60) Provisional application No. 63/827,592, filed on Jun. 20, 2025, provisional application No. 63/779,692, filed on Mar. 28, 2025, provisional application No. 63/761,547, filed on Feb. 21, 2025, provisional application No. 63/709,289, filed on Oct. 18, 2024, provisional application No. 63/687,689, filed on Aug. 27, 2024, provisional application No. 63/676,145, filed on Jul. 26, 2024.

(51) Int. Cl.
| | |
|---|---|
| *G01N 33/543* | (2006.01) |
| *G01N 33/573* | (2006.01) |
| *G01N 33/58* | (2006.01) |
| *G01N 33/68* | (2006.01) |
| *G01N 33/74* | (2006.01) |

(52) U.S. Cl.
CPC ... *G01N 33/6896* (2013.01); *G01N 33/54306* (2013.01); *G01N 33/54313* (2013.01); *G01N 33/573* (2013.01); *G01N 33/582* (2013.01); *G01N 33/68* (2013.01); *G01N 33/6878* (2013.01); *G01N 33/74* (2013.01); *G01N*

*2333/71* (2013.01); *G01N 2333/912* (2013.01); *G01N 2458/10* (2013.01); *G01N 2800/2835* (2013.01)

(58) Field of Classification Search
None
See application file for complete search history.

(56) References Cited

U.S. PATENT DOCUMENTS

2022/0236282 A1 * 7/2022 Mallick ............... G01N 33/543
2025/0147049 A1 * 5/2025 Bateman ............. G01N 1/4044

FOREIGN PATENT DOCUMENTS

WO     WO 2026/024973          1/2026

OTHER PUBLICATIONS

Ercan-Herbst et al., A post-translational modification signature defines changes in soluble tau correlating with oligomerization in early state Alzheimer's disease brain, Acta Neuropathological Communications, 7:192, 2019, pp. 1-19. (Year: 2019).*
Rodriquez et al., Affinity Chromatography: A review of Trends and Developments over the Past 50 years, J Chromatogr B Analyt Technol Biomed Life Sci, Nov. 10, 2020; 1157, pp. 1-41. (Year: 2020).*
Aksel et al., "High-density and scalable protein arrays for single-molecule proteomic studies", doi.org/10.1101/2022.05.02.490328, (2022).
Dunphy et al., "Current methods of post-translational modification analysis and their applications in blood cancers", Cancers, vol. 13(8):1930 (2021).
Ercan et al., "A validated antibody panel for the characterization of tau post-translational modifications", Molecular Neurodegeneration, vol. 12:1-19 (2017).
Guha et al., "Analysis of Tau heterogeneity and proteome-wide changes in Alzheimer's disease at the signle-molecule level", Alzheimer's & Dementia, vol. 19(S12):1-3 (2023).
Joly et al., "Large-scale single-molecule analysis of tau proteoforms", bioRxiv, XP093311366, retrieved online at: https://www.biorxiv.org/content/10.1101/2025.06.26.660445v2, pp. 6-40 (2025).
International Search Report and Written Opinion in application no. PCT/US2025/039113, mailed on Jan. 23, 2026, in 19 pages.

* cited by examiner

*Primary Examiner* — Gary Counts
(74) *Attorney, Agent, or Firm* — Knobbe, Martens, Olson & Bear LLP

(57) ABSTRACT

Methods, reagents, kits and systems for analyzing different proteoforms of proteins of interest are provided. The provided methods, systems, etc. provide detection, characterization and quantitation of proteoforms for different biologically relevant proteins for monitoring and characterizing biological processes.

23 Claims, 25 Drawing Sheets https://doi.org/10.1016/j.cell.2020.10.029

| Frontal temporal dementia model | Genotype | Maturity |
|---|---|---|
| Isogenic ctrl | WT/WT | 3 months |
| Isogenic ctrl | WT/WT | 6 months |
| Mutant | WT/V337M | 3 months |
| Mutant | WT/V337M | 6 months |

| Model of early neurodegeneration | Genotype | Maturity |
|---|---|---|
| Isogenic ctrl | WT/WT | 3 months |
| Isogenic ctrl | WT/WT | 6 months |
| Mutant | WT/IVS10+16 | 3 months |
| Mutant | WT/IVS10+16 | 6 months |

Figure 11

SYSTEMS, METHODS AND COMPOSITIONS FOR ANALYSIS OF PROTEOFORMS

RELATED APPLICATIONS

This application claims priority to each of Provisional U.S. Patent Application No. 63/676,145, filed on Jul. 26, 2024, Provisional U.S. Patent Application No. 63/687,689, filed on Aug. 27, 2024, Provisional U.S. Patent Application No. 63/709,289, filed on Oct. 18, 2024, Provisional U.S. Patent Application No. 63/761,547, filed Feb. 21, 2025, Provisional U.S. Patent Application No. 63/779,692, filed Mar. 28, 2025, and Provisional U.S. Patent Application No. 63/827,592, filed Jun. 20, 2025, the full disclosures of which are hereby incorporated herein by reference in their entirety for all purposes.

BACKGROUND

Biological researchers are constantly seeking better ways to look into the functions of living things, in order to understand the keys to life and health, the causes of disease and dysfunction, and to help identify possible paths of intervention or influence to achieve better outcomes for all of these.

High throughput, highly sensitive detection and analysis technologies have given rise to great advances in the field of biological research. For example, medical research and clinical diagnostics have seen significant advances resulting from the emergence of high throughput technology platforms that routinely decode the human genome or human transcriptome in a matter of hours. An individual's genome, as a blueprint for the components of a given biological system, can provide some insights into development, behavior, risk of disease, responsiveness to therapeutic treatments, longevity and many other characteristics. As such, the genome can provide a powerful source for evaluating risk and predicting outcomes to certain treatments or medications.

Likewise, an individual's transcriptome is the collection of RNA transcripts that are expressed from the genome. The RNA transcripts are, in turn, translated into proteins which may, in some cases, be further modified post translationally. The proteins function as the workhorses that perform the biological functions in biological systems as instructed by the genome. In some cases, characterization and quantification of the transcriptome can lead to clinically relevant diagnoses or prognoses for a given biological system, e.g., a patient.

The advent of high-throughput, relatively inexpensive and routine genetic analysis tools and processes has made genomic or transcriptomic analysis a convenient starting analysis in looking at biological functions. Unfortunately, however, these analyses are really directed at proxies for actual biological function. The genome, for example, is a snapshot of a blueprint, in many cases, taken at conception, that provides very little insight into the present functioning of a biological system. The transcriptome, on the other hand, provides a more contemporaneous measure of that biological function, but still falls short of actual biological operations beyond a measure of what genes are transcribed and when. The information provided, again, is removed from the actual biological functions being carried out at any given moment in time within the biological system, and as a result, in many cases, provides inadequate diagnostic or prognostic precision to guide treatment.

To gain more insightful views into the function, dysfunction and manipulation of biological systems, researchers need analytical systems and methods that measure the actual biological operations that occur within these biological systems, including looking at the presence, prevalence, flux and function of the various proteins within those systems. The set of proteins present within a given biological system is generally referred to as the proteome of that system.

While identifying and quantifying the various proteins in a biological system at any given time potentially yields significant amounts of information as to the functioning of that system, protein presence, absence or quantity alone are not the only key pieces of information. In particular, many proteins within a given proteome function differently, are removed from the system, or engage in or cause myriad different interactions based upon the particular form of the protein that exists. In particular, proteins may be subjected to post translational modifications that result in phosphorylation, glycosylation, truncation, aggregation, or other modifications that can alter the protein's function(s), subcellular location, degradation or post translational cleavage, longevity or how it interacts with other aspects of the system. Similarly, pre-translation modifications to proteins, such as splice variants, that may include excised portions of transcribable genes, can yield proteins that differ from full-length gene products, and as a result, function differently. Any given protein species may exist as different molecules that are each modified in a potentially large number of different ways. The collection of these various forms of a given protein within a given proteome is generally referred to as the different proteoforms of that protein. And across a given proteome, tens, hundreds, thousands or more proteins may each exist as multiple different proteoforms. Scientists are just beginning to gain an understanding of how different proteoforms can produce dramatically different outcomes within biological systems. For example, differentially phosphorylated versions of the microtubule-associated protein tau (or "Tau", for short), which generally functions to stabilize the structure of neurons in the brain, has been associated with the formation of amyloid plaques in the brain tissue of patients suffering from Alzheimer's Disease, and is believed to play a key role in progression of the disease. Accordingly, it is highly desirable to provide methods, systems and reagents for use in being able to accurately and sensitively characterize and quantify a variety of different proteoforms within the proteomes of biological systems. Unfortunately, many existing technologies for analyzing proteins, such as protein or peptide sequencing technologies, mass spectrometry methods, and the like, lack the ability to both comprehensively characterize and quantify proteoforms at high throughput and high sensitivity. The present disclosure addresses these and many other needs.

SUMMARY

Described herein are improved methods, processes, systems, components, and reagents useful in analyzing proteoforms from biological samples. These improvements yield more sensitive, reproducible analysis of proteoforms of a variety of different proteoforms of proteins of interest, e.g., proteins and proteoforms that are of biological relevance/interest in biological research, diagnostics and therapeutics.

Generally speaking, provided herein are methods, processes, systems, devices and reagents that are useful in characterizing different proteoforms of any of a variety of different proteins of interest that include individually assessable proteins including the proteins of interest that may be individually interrogated using affinity reagents specific for one or more characteristics of different proteoforms of the proteins of interest, and identifying those proteins of interest which possess such characteristics based upon the binding of such affinity reagents. The different proteoforms are then characterized based upon the different proteoform characteristics that are identified.

In certain aspects methods are provided for analyzing proteins in a first sample, by providing a population of individual protein molecules from the sample wherein the individual protein molecules are individually addressable, and wherein the population of individual molecules comprises a plurality of individual molecules of a first protein of interest. Proteoforms of the first protein of interest represented by each of the plurality of individual molecules of the protein of interest may be identified based upon identification of a presence or absence of at least a number of different modifications within each of the individual molecules of the protein of interest. From the identified proteoforms, one may characterize a plurality of proteoforms of the first protein of interest present in the sample.

In another aspect, provided herein are methods of analyzing proteins in a first sample, by providing a population of individual protein molecules from the sample wherein the individual protein molecules are individually addressable, and wherein the population of individual molecules comprises a plurality of individual molecules of a Tau protein. Proteoforms of the Tau protein represented by each of the plurality of individual molecules of Tau protein are identified based upon identification of a presence or absence of a number of different modifications within each of the individual molecules of the Tau protein. From the identified modifications on the individual Tau protein molecules, a plurality of proteoforms of the Tau protein present in the sample may be characterized.

In still other aspects, methods are provided for analyzing a sample, by characterizing and quantifying a first proteoform of a first protein of interest in a first sample, and characterizing and quantifying at least a second proteoform of the first protein of interest in the first sample, to provide a proteoform abundance profile for the protein of interest in the first sample.

Also provided herein are systems for characterizing proteins, which comprise one or more solid supports comprising molecules of Tau protein immobilized thereon, wherein individual molecules of Tau protein are individually addressable. The systems may also include a source of a library of a plurality of different affinity reagents where each different affinity reagent has a binding affinity to a Tau protein having a different modification. Also included in these systems is a fluidic system for delivering the plurality of different affinity reagents to the one or more solid supports to contact the affinity reagents with the individual molecules of the Tau protein. These systems also comprise a detector for detecting whether each of the different affinity reagents binds to individual molecules of the Tau protein, and a processor programed to characterize proteoforms of the Tau protein present on the one or more solid supports from detected binding or nonbinding of the different affinity reagents to the individual molecules of the Tau protein.

In a related aspect, also provided herein are systems that comprise an array comprising a plurality of individual protein molecules deposited on a surface of the array and positioned to be individually addressable, wherein the individual protein molecules comprise a plurality of individual molecules of a first protein of interest, and wherein the plurality of molecules of the first protein of interest comprise at least two proteoforms of the first protein of interest. These systems typically include a library of affinity reagents that comprises a plurality of sources of affinity reagents, where each source of the plurality of sources contains a separate affinity reagent; and wherein each affinity reagent has a binding specificity for a different characteristic of one or more proteoforms of a protein of interest and a detectable label attached to the affinity reagent. As above, these systems typically comprise a fluidic system for delivering affinity reagents from the plurality of sources to the array surface, and a detection system for detecting binding of the affinity reagents to the individual molecules of the protein of interest.

Also provided herein are libraries of affinity reagents that comprise a reagent storage vessel comprising at least 5 sources of different affinity reagents, where each source of the at least 5 sources of affinity reagents comprises a separate affinity reagent, and wherein each different affinity reagent comprises a binding specificity for a Tau protein having a different modification, and a detectable label attached to each affinity reagent.

DESCRIPTION OF THE FIGURES

FIG. 5 schematically illustrates affinity reagent selection criteria designed to target different characteristics of Tau proteoforms as well as recombinantly produced Tau isoform standards.

FIG. 9 shows the detected effects of alkaline phosphatase treatment of phosphorylated tau proteins FIG. 10 schematically illustrates systems useful for the analysis of proteins and proteoforms.

FIG. 11 shows information about organoid samples.

DETAILED DESCRIPTION

I. General

Figure 1:
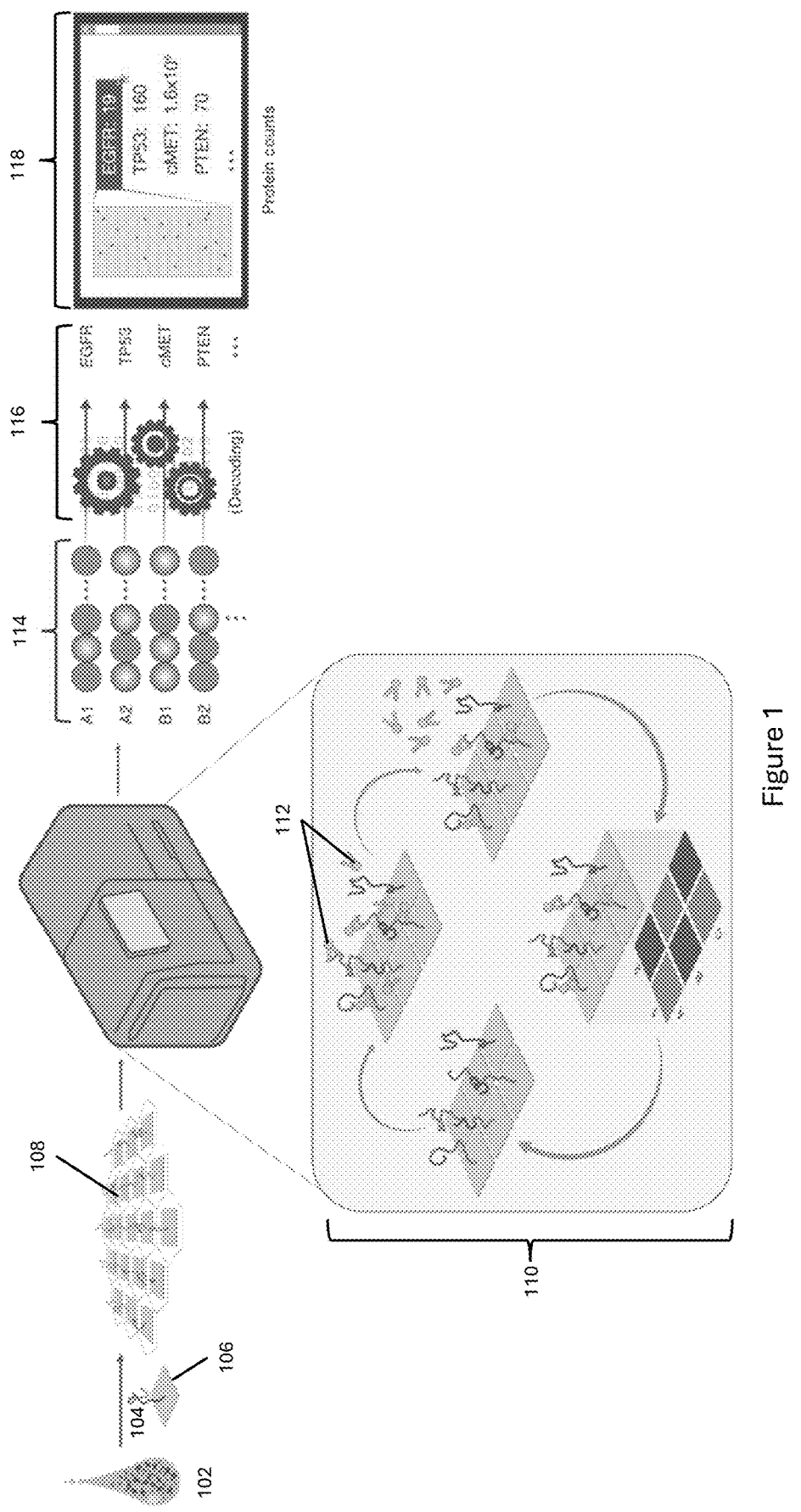
FIG. 1 schematically illustrates a protein analysis process and system.

Provided herein are methods, reagents, systems and processes for use in analyzing and characterizing proteoforms from biological samples. Proteoforms typically refer to the potential various states of a given protein or set of proteins within a biological system, where such states may be defined by one or more of transcriptional or translational modifications or variations in such protein, and/or post translational modifications made to such proteins, including such modifications as post translational cleavage, degradation, phosphorylation, aggregation, acetylation, glycosylation (e.g., N and O linked glycosylation), amidation, hydroxylation, methylation, ubiquitylation, sulfation, or any of a host of additional alkylation, acylation, lipidation, disulfide, iodination amino acid addition, or other modifications made to protein molecules or their constituent amino acid side chains or terminal groups. Within a sample, a particular protein species may exist in multiple different proteoforms, i.e., having different modifications or patterns of modifications.

In some cases, the methods, reagents, systems and processes described herein may be used to identify and characterize proteoforms of a single type of protein, whereas in other cases, the proteoforms of multiple different proteins may be characterized from a single biological sample and system.

In accordance with the methods described herein, in certain cases, analysis of proteoforms begins with the isolation of individual protein or polypeptide molecules in a manner that allows for their individual interrogation and analysis at the single-molecule level. In particular, by analyzing individual, intact or undigested protein molecules of a proteoform, one can more accurately identify which proteoforms are present within a given sample, as well as provide relative quantification of those proteoforms in that sample.

In general, individual protein molecules within a sample may be isolated and made individually addressable by immobilizing them on a solid support. In some cases, this may include isolation of an individual protein molecule of a sample on a bead or particle that may be individually interrogated and analyzed, while in other cases, individual protein molecules may be immobilized on different locations in a solid surface of an array, such that the different locations may be individually interrogated and separately analyzed, e.g., individually addressable.

One example of an array-based approach for protein analysis uses the approach described in, e.g., U.S. Pat. Nos. 10,473,654B1, 11,545,234B1, and Eggertson, et al. bioRxiv (doi.org/10.1101/2021.10.11.463967), the full disclosures of which are hereby incorporated herein by reference in their entirety for all purposes where individual protein molecules are coupled to the surface of an array in separate, optically resolvable locations. The individual proteins are then iteratively probed using detectable affinity reagents that bind to identifiable traits of the proteins, such as specific compositional components, e.g., specific amino acid sequences or sequence contexts. These bound affinity reagents may then be detected, indicating the presence of that particular identifiable trait in the protein or polypeptide that is immobilized at that location.

For example, in the general proteome analysis methods described herein, affinity reagents used are capable of binding to small subunits of the proteins, like trimers or tetramer epitopes (3 or 4 amino acid segments) or other short or small sequence contexts of the protein. These reagents are iteratively contacted with the immobilized proteins on the array surface under conditions where affinity binding can occur. Once the reagents bind to proteins on the array and background reagents are washed away, the bound affinity reagents may be detected, typically through a detectable label group associated with the affinity reagent, such as a fluorophore. Binding of the labeled affinity reagent at a given location on the array indicates the likely presence of the particular epitope in the protein at that location. By iteratively probing using different affinity reagents, and assessing the probability associated with the binding events, one can potentially identify each protein that exists at each spot on the array. Moreover, by using affinity reagents that are not highly specific for an individual protein, but instead are capable of binding larger subsets of the proteome, e.g., multiple proteins containing a given trimer or tetramer epitope, one can potentially deconvolute a very large number of different proteins using a comparatively small number of affinity reagents. This "protein identification by short epitope mapping" (or "prism") approach is described in detail in U.S. Pat. Nos. 10,473,654B1, 11,545,234B1, and Eggertson, et al. bioRxiv (doi.org/10.1101/2021.10.11.463967), previously incorporated herein by reference.

FIG. 1 illustrates a high-level overview of a process used for characterizing large numbers of proteins in a sample using the Prism approach described above. As shown, a protein-containing sample 102 is obtained for analysis. Samples for analysis may be derived from any of a wide variety of biological systems, including animal, plant, microbial, viral, or the like. Moreover, samples may be derived from any of a variety of sources within a particular organism. For example, for animal-derived samples, samples may be obtained from tissue, e.g. as cells or cell lysates, organs, organoids, blood or plasma, or cerebrospinal fluids, or any other sources that may have protein profiles of biological interest.

In the context of an array-based approach for analysis, proteins in the sample are treated to attach individual protein molecules 104 to individual particles, such as structured nucleic acid particles or SNAPs 106. Once coupled to their respective SNAPs, the individual protein molecules are deposited and immobilized upon the surface of an array 108, where the SNAPs' size and/or surface binding characteristics result in the individual protein molecules being sufficiently spaced apart that they can be analyzed separately upon the surface of the array. For ease of illustration, arrays are shown with relatively small numbers of isolated proteins. However, it will be appreciated that an array surface may have upwards of 10s of thousands to 100s of thousands, to millions to billions of locations at which individual protein or polypeptide molecules may be located and separately interrogated/detected, e.g., 10,000 or more individual polypeptides, 100,000, or more individual polypeptides, 1,000,000 or more individual polypeptides, 10,000,00 or more individual polypeptides, 100,000,000 or more individual polypeptides, 1,000,000,000 or more individual polypeptides, or even 10,000,000,000 or more individual polypeptides on the surface of the arrays. Examples of this process and the resulting arrays are described in detail in, for example, U.S. Pat. Nos. 11,603,383B1, 11,505,795B1, WO 2023/102336A1, and Aksel et al., BioRxiv (doi.org/10.1101/2022.05.02.490328), the full disclosures of which are hereby incorporated herein by reference in their entirety for all purposes.

As discussed elsewhere herein, because the arrays described herein are comprised of individually addressable molecules of proteins, and in particular, the proteins of interest, they will generally reflect the dynamic ranges of molecules described elsewhere herein, e.g., from 1 to 9 orders of magnitude in relative concentration, which means that an array could include a single molecule of a given proteoform of a protein of interest, while also including 100s, thousands, 10s of thousands, hundreds of thousands, millions or even billions of other molecules, including other proteoforms of the same protein of interest Once created, an array of individual protein molecules may be interrogated (shown in panel 110) with affinity reagents 112 that are capable of binding to relatively short epitopes within the proteins, e.g., trimer, tetramers or other short sequence contexts of amino acids. In certain aspects, such interrogation is carried out iteratively with individual or limited sets of affinity reagents being contacted with the surface of the array 108. As noted previously, by utilizing affinity reagents that may bind to multiple proteins, but not all proteins, one can iteratively narrow down the identity of a protein molecule at any given position based upon the pattern of affinity reagents that bind to the protein at that location. As a result, one may be able to identify tens of thousands of proteins with a far smaller number of affinity reagents than if one were to use only highly specific affinity reagents, e.g., affinity reagents that specifically bind to only one protein. Again, examples of this analytical approach are described in, for example, U.S. Pat. Nos. 10,473,654B1, 11,545,234B1, and Eggertson, et al. bioRxiv, previously incorporated herein by reference.

In process, separate interrogation steps introduce different affinity reagents, or mixtures of affinity reagents, to the surface of the array, as shown in the expanded panel. These reagents are typically labeled, e.g., with fluorescent dyes, so that they may be detected. Following an incubation step to allow affinity reagents to bind to their specific target epitopes, excess reagents are washed away and the surface of the array is scanned using a fluorescence detection system, e.g., a scanning fluorescence microscope, and those points on the array where the affinity reagents are bound are detected and recorded. In some cases, different affinity reagents may be differentially detectable, e.g., by carrying differently detectable labels like fluorescent labels having different emission spectra, so as to allow simultaneous interrogation with 2, 3, 4 or more different affinity reagents. In these cases, the detection system will typically include optics, e.g., filters and directional components, that separate and separately measure signals having different spectral characteristics, thus allowing separate detection of the different affinity reagents bound to the array at the same time. Alternatively or additionally, different probes may be differentially detectable based upon their differing characteristics, e.g., their binding kinetics to target proteins or epitopes, such that one can differentiate two probes binding to the same protein molecule based upon the kinetics of the binding interaction, e.g., on and/or off rates. In such cases, real time observation optics may be employed to monitor binding and release of different affinity probes over time.

Following rounds of interrogation and scanning, the pattern of where different reagents did and did not bind (schematically illustrated at 114, are used to decode which proteins are at which positions on the array. These decoding processes typically utilize probability models (e.g., as schematically represented at 116) to assess the likelihood of true and false positive and negative binding events to ultimately identify individual proteins. At the end of the process, the identities and quantities of each type of protein on the surface of the array may then be determined (as shown at 118), and ultimately extrapolated back to the identity and quantity of different proteins within the sample. Although described in terms of iterative interrogation with individual affinity reagents for ease of understanding, it will be appreciated that interrogation steps may utilize multiple affinity reagents that are capable of separate detection, despite being present in the same analysis. For example, multiple different affinity reagents may be labeled with differentially detectable labels, e.g., fluorescent labels having different emission spectra, fluorescent lifetimes, etc. such that one may differentially detect binding of the different affinity reagents to proteins on the array.

II. Proteoform Analysis

A. Proteoform Characterization

In the context of proteoform analysis, however, the methods described herein seek to identify which proteoforms of particular proteins exist within the sample. Thus, in addition to being able to identify where and how often a particular type of protein is located on the array, and thus, within a sample, using the methods described herein, one can additionally, or alternatively identify which proteoform of that protein is present in each location on the array, and thus in the sample from which the array was created. Additional context for the methods, processes, reagents, and systems described herein may be found in published U.S. Patent Application No. 2022/0236282, International Patent Application Nos. PCT/US24/15132, and WO 2023/038859, the full disclosures of which are hereby incorporated herein by reference in their entirety for all purposes.

For example, in some cases, proteoforms of a particular protein may exist as differently phosphorylated proteins within the same sample, meaning that different proteins may be phosphorylated at different amino acid residues in the protein, and may additionally be phosphorylated at one or more potential phosphorylation sites within the protein. By probing the array (including individually located molecules of the particular protein of interest) with multiple affinity probes that specifically recognize different phosphorylated species of the proteins of interest, e.g., recognizing and binding to the phosphorylated version of a particular epitope within the protein of interest, one can identify which phosphorylated epitopes, if any, are co-located on the array with the proteins of interest. Moreover, since multiple different probing events are carried out for the different phosphorylation sites in such proteins, one can determine the pattern of phosphorylation of each molecule of the protein of interest on the array, e.g., if and where in a protein's amino acid sequence a protein molecule of interest may be phosphorylated. Lastly, by counting the number of molecules representing each of the different patterns of phosphorylation, one can obtain a relative quantification of the different phosphorylated proteoforms on the array, and by extrapolation, in the sample from which the array was created.

While described in terms of phosphorylation, it will also be appreciated that a proteoform of a particular protein may represent more than just a single type of modification, e.g., phosphorylation at one or more sequence locations, but may also include additional different types of modifications, e.g., ubiquitylation, methylation, truncation, or any of the other modifications described elsewhere herein.

As will be appreciated, in many cases, the affinity reagents used for proteoform analysis will have a higher specificity for their targets than those used in the more general proteome analysis methods described above, where more promiscuous probes (i.e., probes that bind to shorter epitopes and thus multiple different proteins) are used. In particular, probes that are highly specific for epitopes that include the given proteoform variation, e.g., phosphorylation site, insertion, etc., may generally be used for proteoform characterization. Such probes may have affinity for larger sequence segments and contexts than those used in proteome characterization. For example, rather than a trimer or tetramer epitope, proteoform affinity reagents may target longer sequence segments and/or contexts, e.g., 5, 6, 7, 8, 9, 10, 15, 20 or more amino acid residues in sequence or in spatial proximity in a protein's three-dimensional structure.

Although discussed in terms of higher affinity probes for proteoform analysis and more promiscuous (or multi-affinity) probes for generalized proteome analysis, it will be appreciated that in either version, the probes used may inform the other analysis, e.g., in a broadscale proteome analysis which identifies proteins one may glean information that is more specific to a particular proteoform that is present. Likewise, where one is seeking to identify the proteoforms of interest present on an array, one may glean broader information about the presence and quantities of proteins on the array, including the protein of interest.

A similar approach may be used to identify proteoforms that represent different splice isoforms or truncations of different protein molecules as well. In particular, one can iteratively probe the protein of interest (and its altered versions) using affinity reagents that target different regions of the protein that may vary among its different forms, e.g., included or excluded exon coded regions, truncated portions, etc., in order to generate a profile of each of the proteins of interest on the array.

In many cases, analyzing and characterizing the proteoforms of different proteins of interest that are present in a sample may involve combinations of the above processes for different types of modifications (e.g., multiple processing modifications and/or different post translational modifications).

Figure 2:
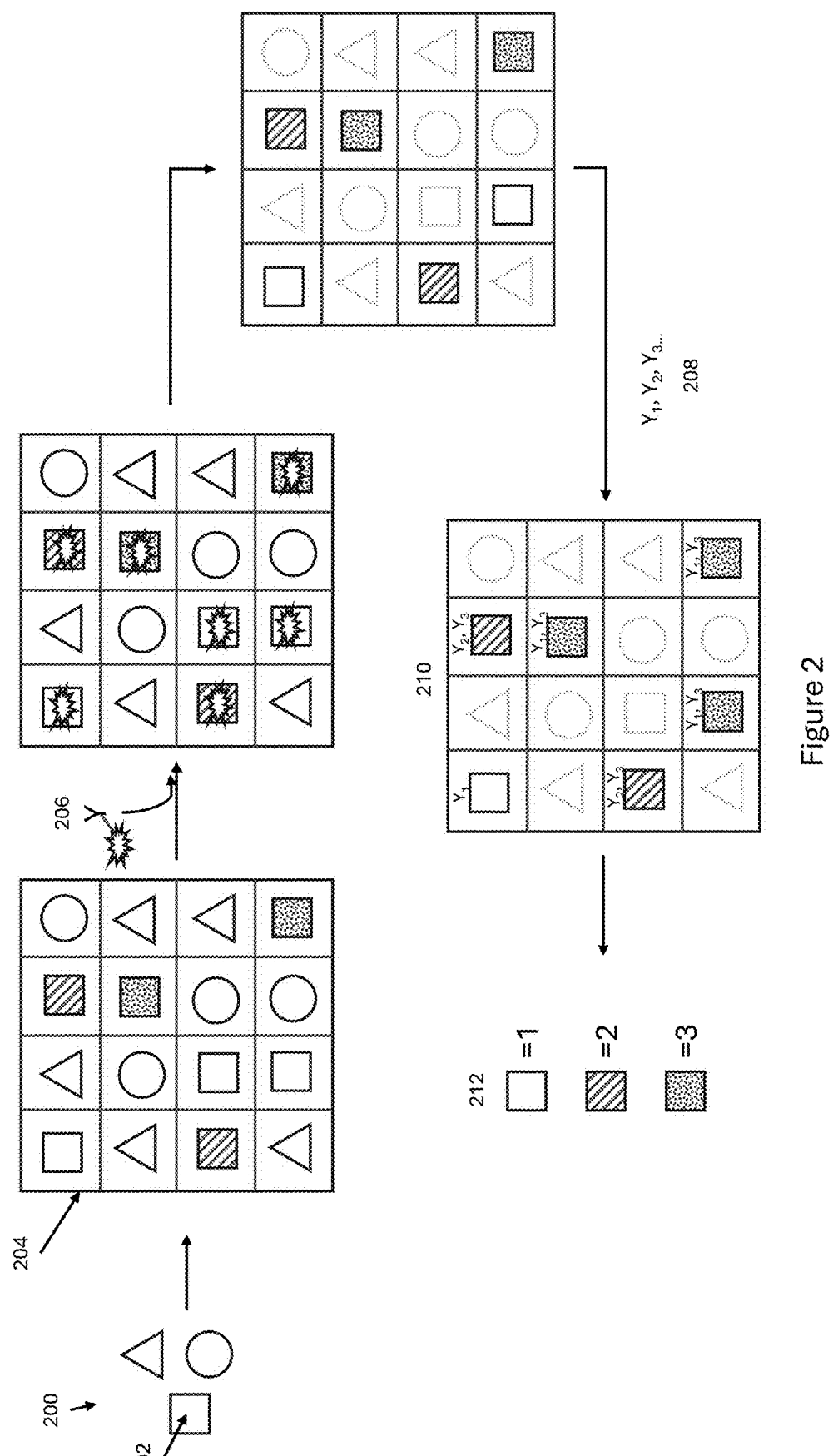
FIG. 2 provides a high-level overview of a proteoform analysis approach.

FIG. 2 illustrates a process used for characterizing proteoforms using the methods described herein. As shown, a set of proteins 200, e.g., from a sample, either with or without enrichment or purification, that includes a particular protein of interest 202 (including its various proteoforms and isoforms) is deposited on the surface of an array 204, such that individual protein molecules are separately immobilized and are separately accessible/detectable. As shown, the surface of the array includes a mixture of proteins, including different forms of the protein of interest 202 (shown as 202a, 202b and 202c).

In some cases, the array may be pre-characterized with respect to the location of particular proteins of interest (including their various proteoforms and isoforms), e.g., using the broadscale protein characterization described above. In other cases, and particularly where one is interested in more targeted analysis of specific proteins of interest and their respective proteoforms, the particular proteins of interest may be identified and located using more specific interrogation techniques, e.g., more highly specific affinity reagents that bind very specifically, and thus identify the proteins of interest on the array. This is shown in FIG. 2, where a labeled antibody 206 specific for all forms of the protein of interest 202 is contacted with the array 204. As shown, binding of this antibody provides an indication of the locations on the array occupied by the protein of interest 202 and its various proteoforms and isoforms, e.g., 202a, 202b and 202c.

In some cases, the affinity reagents used to characterize specific proteoforms, and their associated interrogation steps, may provide the locations on the array where all of the different forms of the protein of interest exist, thus obviating the need for a specific step for identifying all possible locations of the protein of interest. In particular, as will be appreciated, in many cases, the higher specificity affinity probes used may allow one to readily identify the locations of the particular protein(s) of interest on the array without the need for broad-scale proteome decoding first. For example, one may interrogate a protein array with affinity reagents specific for one or more species of the particular protein (or proteins) of interest to identify their locations on the array. Interrogations with affinity reagents that are specific for particular modifications would then be used to assign the different modifications to each specific protein location, to provide a characterization of the particular proteoform represented by each protein of interest on the array.

In process, the array 202 that includes the protein of interest in multiple different proteoforms, e.g., proteoform 202a, 202b and 202c, is interrogated using affinity reagents that are specific for different characteristics that make up the different proteoforms. For purposes of illustration, as shown, the protein of interest 202 may include three possible phosphorylation sites within its sequence, and that it may exist as a different proteoform based upon the combination of such sites that are and are not phosphorylated. The resulting proteoforms may include any one of the three sites being phosphorylated, any two of the sites being phosphorylated, all three of the sites being phosphorylated, or none of the sites being phosphorylated. By iteratively interrogating the individual molecules of the protein of interest using affinity reagents specific for phosphorylation at the different positions in the protein of interest, one can easily identify which of eight possible proteoforms is represented at each site using only three affinity reagents, based upon the proteins to which such reagents bind.

By way of illustration, as shown in FIG. 2, the array surface includes the protein of interest in its various proteoforms and isoforms, e.g., 202a, 202b and 202c is interrogated with a series of different affinity reagents ($Y_1$, $Y_2$ and $Y_3$ in 208), each specific for a different characteristic of the proteoforms of the protein of interest 202, such as phosphorylation at one of the three phosphorylation sites. By identifying where on the array these antibodies bind (e.g., shown at 210), one can attribute the specific characteristic to the protein located at that position on the array, and thus characterize the particular proteoform or isoform that is located at that position. Because the array represents single molecule localization of proteins, one can then simply count the number of each different proteoform present in order to quantify that proteoform and extrapolate that back to the originating sample (e.g., illustrated at 212).

Although described in terms of probing for a given characteristic of different proteoforms once (e.g., exposing an array to an affinity reagent that targets a given characteristic of a proteoform (or proteoforms) of the protein of interest), in certain preferred cases, a particular characteristic may be probed multiple times to increase the certainty of the identification. In practice, for example, one may re-probe an array that includes proteins of interest in the various proteoforms and isoforms multiple times using the same affinity reagent. Alternatively, one may re-probe the array using multiple affinity reagents that may be different but which recognize and bind to the same characteristic. In general, repeated probing or interrogation of an array and the particular proteins of interest with the same affinity reagent, or different affinity reagents with the same target, may be carried out 2, 3, 4, 5, 6, 7, 8, 9, 10 or more times. For example, a particular protein on an array may be probed multiple times using a single type of affinity reagent for a given phosphorylated epitope within that protein. Alternatively, as noted, different affinity reagents that similarly bind to that same phosphorylated epitope may be used to probe the same array of proteins. In certain cases, multiple probing using the same affinity reagent may be performed sequentially, e.g., repeating a particular probing step directly in sequence, e.g., consecutively, following a probing using the same reagent. However, in preferred instances, repeat probing or interrogation with the same reagent (or an affinity reagent targeting the same proteoform characteristic), may be non-sequential or non-consecutive. For example, where a given analysis requires interrogation of an array of immobilized proteins using four different affinity reagents to different target proteoform characteristics, e.g., affinity reagents A1, A2, A3, and A4, one may separate repeat interrogations with the same reagent by interspersing interrogation with one or more different reagents. As such, an exemplary set of interrogation cycles may be: A1, A2, A3, A4, A1, A2, A3, A4 . . . . Likewise, one may simply intersperse a single reagent interrogation, e.g., A1, A2, A1, A3, A1, A4, etc., or even perform such repeated interrogations in random, albeit non-sequential order.

Such multiple probings may increase the confidence in the assessment of binding of an affinity reagent to its expected target epitope.

As will be appreciated, the characteristics of a proteoform may include any of a variety of different types of post-translational modifications, splice variations, degradation products, or the like as described above.

Although described for illustration as analysis and characterization of relatively small numbers of proteoforms for any given protein, the number of possible proteoforms for any given protein will generally be dictated by the number of different potential modifications that may be present in a particular protein. Where a protein may potentially include up to n modifications, the number of possible proteoforms of that protein may be upwards of $2^n$. Where a particular protein species may contain any number of up to 20 different modifications, that protein could potentially have over 1,000,000 different possible proteoforms.

In the context of the methods described herein, it will be appreciated that one may readily characterize a number of proteoforms for a given protein that is related to the number of detectable modifications for that protein, such that where the number of detectable modifications is equal to y, the number of detectable or characterizable proteoforms for that protein could be up to $2^y$. A detectable modification will typically include an epitope the presence or absence of which may be detected, e.g., using the methods described herein, such as epitopes including modified amino acids, truncated or missing epitopes, or the like. In accordance with certain aspects, the methods described herein may use affinity reagents that are specifically able to recognize and bind to such epitopes, allowing one to assess whether they are present or absent in a given protein molecule.

Again, by way of example, where one possesses a library of affinity probes that is capable of characterizing, for example, 12 different modifications to a particular protein species of interest, one would be able to characterize up to $2^{12}$ different potential proteoforms of that protein of interest in a given sample. While the limits of the potential number of proteoforms of any particular protein, or one's ability to detect all possible modifications, may vary, it will be appreciated that for many applications, a predetermined and smaller number of modifications may be deemed more critical for the research at hand. Accordingly, in many cases, one may seek to detect smaller numbers of modifications in a given protein species of interest than are theoretically possible. For example, in many cases, one may simply wish to detect proteoforms that represent patterns of the presence or absence of 1, 2, 3, 4, 5, 6, 7, 8, 9, 10, 11, 12, 13, 14, 15, 16, 17, 18, 19, 20, 30, 40, 50, 60, 70, 80, 90, 100 or more different potential individual modifications to the protein species of interest. As noted above, the number of proteoforms of a given protein of interest increases substantially exponentially with the number of modification sites within that protein, and can readily include anywhere from 2 proteoforms to well over a million proteoforms (with the caveat that a modification that results in a truncation of a protein of interest may in fact delete residues at which other modifications could occur in the full length protein, and thus potentially reduce the theoretical maximum possible number of modifications). The foregoing is illustrated with reference to FIG. 13 in which 8 different modification site specific antibodies were used to characterize the proteoforms present in the samples analyzed, and FIG. 15, in which 7 different modification site specific antibodies, were used to characterize the proteoforms present in the samples analyzed, which provided the ability to assess up to 265 and 128 different proteoforms of the Tau protein, respectively.

While described above in terms of the possible numbers of modification patterns or proteoforms that could exist in a given protein of interest, given all possible modifications, in biological systems, the number of proteoforms of a given protein of interest may actually be less than the theoretical maximum.

In accordance with the methods, processes, reagents and systems etc. described herein, analysis, characterization, identification and/or quantification of proteoforms of a protein of interest may include individual or separate proteoforms that include all possible modifications to a protein of interest, or it may include proteoform groups that each share a common pattern of a subset of all possible modifications to the protein of interest. In particular, in many cases, one may be desirous of analyzing a subset of modifications in any given protein of interest, e.g., focusing on a pattern of modifications that represents a subset of all possible modifications to the protein of interest that have demonstrated clinical relevance or are otherwise of significant scientific interest. By way of example, for illustration purposes, a given analysis may examine a group of modifications A through E to a given protein of interest, where that protein may have additional possible modifications F through Z. In such cases, identification of a proteoform (or proteoform group) having modifications A through E may include a number of different individual proteoforms that share this same pattern, but differ with respect to potential modifications elsewhere. Thus, for purposes hereof, analysis, detection, quantification of a given proteoform may relate to such analysis, detection and quantification, etc., of a group of proteoforms that share the common pattern of modifications, while still being heterogenous with respect to the other modifications, e.g., F through Z.

Relatedly, in some analyses, one may be focused on characterizing a subset of proteoforms in a protein of interest that represents a fraction of the total possible number of proteoforms for that protein, given its different possible biological modifications (e.g., splice forms, PTMs). Similarly, where one utilizes an affinity probe library that is capable of identifying a subset of modifications to a given protein of interest, one may still wish to further focus analysis on a subset of all possible proteoforms that would be characterizable using that set of affinity reagents. In some cases, the subset of possible proteoforms that are characterized may simply relate to those that are actually present within the biological systems, e.g., the particular system just does not create certain modification patterns in any detectable amount. In other cases, certain specific patterns may be identified as being of particular clinical or experimental relevance, e.g., specific proteoforms or proteoform changes being highly correlated and/or causative of specific clinical outcomes. Such proteoforms may reflect significant numbers of modifications (or absence of modifications) in any given protein molecule, but could be focused only on 1, 2, 3, 4, 5, 6, 7, 8, 9, 10, 20, 30, 40, 50, 60, 70, 80, 90, 100 or more such different proteoforms, or focused on less than 100, less than 90, less than 80, less than 70, less than 60, less than 50, less than 40, less than 30, less than 20, less than 15, less than 10, less than 9, less than 8, less than 7, less than 6, less than 5, less than 4, less than 3, or even only 2 such patterns, despite the potential of much larger numbers of possible proteoforms for that protein. As will be appreciated, the foregoing description specifically includes ranges bounded by the foregoing numbers in relevant combination, e.g., 2 or more patterns and less than 100 patterns, etc.

In some cases, an analysis will only seek to characterize less than 90%, less than 80%, less than 70%, less than 60%, less than 50%, less than 40%, less than 30%, less than 20% or even less than 10% of the total possible number of proteoforms for a set of possible modifications to a protein of interest, whether that set of modifications constitutes all possible modifications or just all possible detectable modifications given the affinity reagent panel used.

With respect to the methods described elsewhere herein, focusing an analysis in accordance with the foregoing may include providing only affinity reagents that are capable of characterizing the reduced number of proteoforms, e.g., foregoing detection of certain irrelevant modifications. Alternatively or additionally, such reduced analyses may utilize bioanalytic processes in decoding the detected proteoforms that ignore less relevant or biologically absent proteoforms.

By way of example, in some cases, one may be focused on the relative abundance of a single particular proteoform or set of proteoforms, e.g., a triple phosphorylated species of a given protein, that may or may not also include other modifications, splice or truncations, etc. vs. any other proteoform of that same species. Alternatively, or additionally, one may be focused on characterizing the relative abundance of a particular proteoform or set of proteoforms with that of potential precursor species, e.g., proteoforms showing double or single phosphorylated species. In other cases, one may look to characterize the relative abundance of hyper-phosphorylated species, e.g., triple or quadruple phosphorylated species of the proteins of interest, as indicators of disease onset, progression or severity.

In some cases, a protein-containing sample may be processed to isolate the individual protein molecules contained in that sample, e.g., on the surface of an array as described above. In one part of the process, e.g., in an initial step in the process, the particular protein molecule at each location on the array may be identified using a whole proteome analysis technique, such as Prism, as described above. Once the proteins are identified at each location, one can then interrogate the proteins for the different proteoforms using probes that are specific for different proteoforms of the proteins of interest. For example, a protein-containing sample may be analyzed to identify the full range of proteins in that sample, including certain specific proteins of interest that are known to exist in biologically relevant proteoforms. One can then further analyze those specific proteins in those locations on the array to identify and potentially quantify the different proteoforms of that protein on that array, quantifying both the different proteoforms as a fraction of the amount of the protein of interest and as a fraction of the overall proteome present in the sample.

In other cases, a protein of interest may not be present in a sample at levels that are easily analyzed, e.g., they may be below levels where one can assure a representative isolation of such proteins on an array/flow-cell. In these instances, it can be advantageous to enrich for the proteins of interest prior to depositing them onto the array, in order to subsequently analyze the different proteoforms present within the population of such protein's molecules in the sample. Enrichment can be accomplished using a number of conventional means, including chromatographic enrichment or purification, using any of size exclusion, charge-based separation, relative hydrophobicity, or even using affinity chromatography, to separate and enrich for the protein of interest. In some cases, immune-precipitation techniques, where antibodies to the protein of interest are coupled to beads or other particles, may be used to selectively pull the protein of interest out of solution. The beads are then washed and the protein of interest is then eluted from the beads into a separate fluid, typically at a higher concentration and/or purity than the sample from which it was obtained. In some cases, immune-enrichment may involve the use of multiple different antibodies that target and bind to different portions of the protein of interest. This is particularly the case where the protein of interest may exist in multiple different isoforms that may include or lack different portions of the full-length protein, e.g., as a result of splicing variations, post-translational processing or degradation, or the like. By using antibodies that target the different regions reflected in those different isoforms, one can target and isolate a larger fraction of all of those isoforms and modified proteins. These antibodies may be used as a pool or in tandem during immunoprecipitation. In the case of immunoprecipitation using bead-bound antibodies, these antibodies may again be immobilized on the beads separately where the beads are pooled prior to use in the immunoprecipitation step, or they may be pooled prior to immobilization on the beads (see e.g., FIG. 7).

In some cases, enrichment of the protein of interest may employ a bead-based immunoprecipitation technique where antibodies or antibody binding fragments that are capable of specifically binding to the protein of interest are coupled to solid supports or beads using conventional techniques. These beads are then suspended in a liquid sample containing the protein of interest which are then bound by the antibodies attached to the beads. The beads are then washed to remove any unbound proteins or other materials. The effectiveness of these beads in capturing protein of interest from a mixture can be monitored by a semi-quantitative Western Blot, where a serial dilution of recombinant protein is used as a standard, and the signals from samples before and after immune precipitation can be compared. The specificity of the immunoprecipitation can be examined by using negative controls such as naïve mouse IgG, which would not be expected to cause depletion of the protein of interest. Effectiveness can also be examined by gel staining of the proteins that are enriched by the beads using well established methods like SDS-PAGE followed by Coomassie and silver staining.

Following binding to the beads, the beads may then be subjected to a changed environment in which the binding is weakened. For example, in some cases, the beads may then be exposed to a competitive binder for the antibodies, such as a polypeptide that mimics or duplicates the binding domain or epitope of the protein of interest to competitively elute the proteins of interest from the beads. While other conditions may also be employed for elution, including for example, changes in salt concentration, pH etc., this type of elution allows for a more focused elution for the protein of interest as opposed to more stringent conditions that tend to remove a wider variety of specific and non-specifically bound materials from the beads. A variety of different competitive binders may be employed in the context of this type of elution, including poly or oligopeptides, peptide mimics, or other specific binding inhibitors for the antibodies used in the enrichment process. In some preferred cases, these competitive binders may include synthetic peptides designed to mimic or duplicate the sequence of the target epitope of each antibody that was used in the enrichment process, which peptides may be used in molar excess to the antibody. Where, as noted previously, multiple different antibodies having different target epitopes are used in ensuring full enrichment of the protein of interest (and its various proteoforms and isoforms), likewise, multiple mimetic peptides or other competitive binding reagents may be included in the elution process.

Depending on the purity of the bound material and the requirements of the analysis, other nonspecific binding inhibitors, commonly used in disrupting protein-protein interactions, may also be used in the elution of the protein of interest from the beads, such as ionic detergents, low pH buffers, chaotropic salts and other denaturants, etc.

In optional cases, additional sample preparation steps may be carried out on the proteins of interest while they are bound to the beads, in order to utilize the advantages of support-bound proteins of interest, e.g., in subsequent purification and/or separation steps. For example, in some cases, following binding of the protein of interest to the beads, the bound proteins may be exposed and coupled to the nanoparticles, e.g., SNAPs, used to deposit the proteins of interest in different locations on an array surface. By performing this step on bead-bound proteins of interest, one can more effectively remove free particles, i.e., particles that have no associated proteins of interest, through a simple washing step versus a subsequent more complex separation process, e.g., chromatography, filtration, etc.

By employing a single process step as outlined above for both immuno-isolating a protein of interest and coupling such protein to its SNAP, one can analyze far smaller concentrations of a protein of interest in a sample than would be attainable using a multiple step process where losses at each step rapidly deplete the measurable amount of protein of interest in the analyzed sample. For example, in some cases, where a protein is first enriched using a bead-based immunoprecipitation process, where bead-bound proteins are eluted and then coupled to SNAPs, it can result in sizable losses at each stage. In one exemplary process, volume requirements, as well as the need for excess proteins and particles needed to drive the proper coupling reactions necessitated a significantly larger starting sample input than would be ideal. For example, where a protein of interest makes up about 0.3% of the mass of a particular type of sample tissue, input sample size may need to be in excess of 400 ug of starting tissue lysate (sample input), to yield a final quantity of protein of interest to analyze using the methods described herein, e.g., in the femtomole or sub-femtomole range. Relatedly, where concentrations are even less, sample inputs become increasingly untenable, e.g., due to a lack of sufficient tissue, etc. However, using the single step processes described above, one can use sample inputs of the protein of interest that are far lower, and are at or below 1 ug, 500 pg, 250 pg, 100 pg, 50 pg, 10 pg, 5 pg, 2 pg, 1 pg, 500 ng, 400 ng, 300 ng, 200 ng, 100 ng, 50 ng, 40 ng, 30 ng, 20 ng, 10 ng or even lower, as well as amounts between any two of the foregoing quantities. In any event, measurable amounts of a protein of interest in a sample input may be between 1 ng and 1 ug, between 5 ng and 100 pg, between 5 ng and 5 pg, between 5 ng and 500 ng, between 5 ng and 50 ng, between 10 ng and 1 pg, between 10 ng and 100 ng, and between 10 ng and 50 ng of protein of interest in the starting sample input.

As will be appreciated, when subject to an enrichment step, it may be more difficult to quantify the amount of different proteoforms present in the original sample as a result of the concentration that occurs during the enrichment step for the protein of interest. Accordingly, in some cases, standards may be included in the sample, prior to the enrichment step to provide a basis for tracking how much protein was present originally and how that was impacted by the enrichment step. For example, in some cases, a known amount of the protein of interest, that is separately identifiable from the endogenous protein of interest, may be spiked into the sample. By tracking the standard or control protein through the process and quantifying what was detected at the back-end, one can extrapolate a similar partitioning of the endogenous protein of interest, and thus get a relative quantification of such protein in the original sample. Providing the protein of interest as a separately identifiable control can be a matter of adding a detectable label or tag to such a standard protein in order to later identify it during the analysis process. In some cases, different proteins, i.e., not the protein of interest, may be employed as standards for tracking the various steps, e.g., enrichment, deposition, etc. Such tags may include chemical tags that may be modified to be detected, fluorescent tags that may be detected using fluorescence microscopy, or biochemical tags that may be recognized by specific probe moieties, e.g., antibodies, or other highly specific binding groups, such as biotin or streptavidin, such that the standard version of the protein may be identified and distinguished from the protein of interest that originates from the sample. Alternatively, rather than adding standard proteins to the sample material, one may also optionally run parallel analyses using standard "samples" where the amount of the protein of interest is known. Based on the yield of the standard process, one can make an assumption that the true sample was processed with similar yields. As will be appreciated, one could potentially run multiple "standard samples" that included different amounts of the protein of interest in order to create a quantity curve in order to even better assess the abundance of the protein of interest in the true sample.

B. Proteoform Pattern Characterization and Monitoring

The proteoform characterization methods and systems described herein are particularly useful in characterizing broader patterns of proteoforms present in a given sample or across multiple samples. In particular, for many proteins, there exist numerous potential modifications at numerous different sites within the protein or of numerous different types, including e.g., splice variations. As these may exist alone or in any number of combinations, a number of different proteoforms may exist in a given sample for a given species of protein at any given time. In some cases, the different patterns of proteoforms in a sample (presence, quantity, relative abundance, etc.) may have different and important implications related to the function of the biological system from which the sample was derived.

The functionality of the methods, processes, systems and reagents described herein provides an apt analogy of the complexity of proteoforms in biological systems. In particular, the methods, processes, systems and reagents described herein are capable of characterizing multiple levels of exponentiation of biological complexity related to proteins and proteoforms that have previously been unmeasurable.

For example, at a first level of complexity, and as described in detail herein, one may readily detect modifications at numerous sites within a molecule of a particular protein of interest from a sample to derive a pattern of modifications (or proteoform) within that protein. In a further level of complexity, one may ascertain multiple patterns of modifications (or proteoforms) across multiple molecules of the particular protein of interest from a sample. In still another level of complexity, using the platform described herein, one may readily quantify each of those proteoforms in a sample to provide relative abundances of each. As an added complexity, one may further ascertain and compare the proteoforms present and their relative abundances across multiple samples, to compare shifts in those patterns and/or their relative abundances between different samples, e.g., healthy vs. diseased, a given patient's samples from different times, samples pre and post treatment or intervention (or hypothesized intervention), etc. Lastly, given the broad sensitivity of the platform described herein, one could do all of the foregoing with multiple different proteins of interest.

As described above, for any given protein of interest, the methods described herein are readily able to characterize the presence or absence of 1, 2, 3, 4, 5, 6, 7, 8, 9, 10, 11, 12, 13, 14, 15, 16, 17, 18, 19, 20, 30, 40, 50, 60, 70, 80, 90, 100 or more different modifications within a protein of interest. The detected modifications within a given molecule of a protein of interest make up a pattern of modifications to that protein, or a proteoform, that is present in the sample analyzed. By detecting these modifications across multiple molecules of the protein of interest in the sample, one can characterize multiple patterns of modifications or proteoforms of the protein of interest that are present in the sample. In particular, as noted previously, for a given protein of interest, one may readily characterize from 1 to millions of different proteoforms of a protein of interest, but in preferred cases, may characterize 1, 2, 3, 4, 5, 6, 7, 8, 9, 10, 20, 30, 40, 50, 60, 70, 80, 90, 100 or more differing proteoforms of the protein of interest, or less than 100, less than 90, less than 80, less than 70, less than 60, less than 50, less than 40, less than 30, less than 20, less than 15, less than 10, less than 9, less than 8, less than 7, less than 6, less than 5, less than 4, less than 3, or even only 2 such patterns, with the foregoing description including ranges between any two relevant numbers provided, e.g., 2 or more and less than 100 different proteoforms, etc.

In some cases, the mere presence or absence of different proteoforms in a sample, or over time in a biological system, may provide only one aspect of important information. In many cases, a biological system may maintain some, many or all of the same proteoforms during periods of biological change, but the ratios of the abundances of different proteoforms present at any given time may change and be reflective of biological change. For example, a healthy patient's sample may reflect a pattern of proteoforms for a given protein of interest where the different proteoforms are present in the sample at a first set of abundance ratios, whereas the same proteoforms present in a diseased patient's samples may be present at measurably different abundance ratios, indicating the diseased state. Moreover, by monitoring a patient over time and examining these ratios, one may be able to identify inflection points in the potential onset of disease in otherwise healthy patients. For example, by characterizing and quantifying the various different proteoforms of one or more proteins of interest in a sample, one can develop a pattern or set of ratios of proteoform abundances in that sample, and compare that pattern of proteoform abundances to other samples, e.g., healthy vs. diseased patient samples, monitored patients over time, treated and untreated samples, e.g., for identifying candidates for disease prevention or intervention, etc.

Accordingly, in addition to being able to characterize which proteoforms of a given molecule of interest are present in a sample, using the methods, processes, systems and reagents described herein, one can also quantify the amounts or relative abundances of each proteoform present in a given sample. In addition, because the methods described herein characterize the proteoforms on a single molecule basis, one can potentially quantify the number of protein molecules that represent each of the various proteoforms of the protein of interest are present at extremely high dynamic range, e.g., measuring abundances of different proteoforms over 9 orders of magnitude, or from, e.g., 1 molecule to billions of molecules or even greater. By way of example, one may measure different proteoforms within a sample where the relative abundances between any two proteoforms in the sample may differ by less than 1 order of magnitude, more than 1 order of magnitude, more than 2 orders of magnitude, more than 3 orders of magnitude, more than 4 orders of magnitude, more than 5 orders of magnitude, more than 6 orders of magnitude, more than 7 orders of magnitude, more than 8 orders of magnitude, or more than 9 orders of magnitude.

As will be appreciated, the significant detection dynamic range of the methods and processes described herein provides significant advantages in detecting and quantifying rare proteoforms of any given protein of interest among populations of potentially hundreds, thousands, 10s of thousands, 100s or thousands, millions, or even billions of other proteins, including other proteoforms of the proteins of interest.

Based upon the relative abundances of the different proteoforms present in a sample, one may provide a proteoform abundance profile of the sample that includes characterization of a plurality of different proteoforms present in that sample (as described above), and the relative abundances of each such proteoform (as also described above). From these proteoform abundance profiles, one may make comparisons among different samples to ascertain changes in biological functions, conditions, etc. impacting those samples. Accordingly, one may compare the proteoform abundance profiles of 2, 3, 4, 5, 6, 7, 8, 9, 10, 20, 30, 40, 50, 60, 70, 80, 90, 100, 200, 300, 500, 1000, 10,000, 100,000, 1,000,000, 5,000,000, 10,000,000, 100,000,000 or more different samples, where such samples may be derived from individual sources or patients, may reflect multiple different sources or patients, may reflect different time courses, different experimental variables, different treatments, or different interventions in biological systems and/or may be derived from biological organisms, model cellular or in vitro systems, or any other source of biological material relevant to the analysis being performed.

In analyzing, characterizing and comparing proteoforms, including proteoform abundance profiles, from multiple samples, certain patterns may emerge as being particularly relevant in the transition of the biological system from which they are derived. For example, the emergence of a particular pattern (appearing or disappearing proteoforms, shifts in proteoform abundance profiles, etc.) may signal the onset of a disease or the transition of a disease state in a patient. The pattern may reflect a particular order of modifications that occur in order for that transition to take place, e.g., a modification at a specific residue that precedes modification at a second specific residue, an increase in a particular proteoform abundance that precedes an increase in another, etc. that signals transition from one state to another. In such cases, comparison of patterns may look to characterize whether such patterns occur as a means of diagnosis, or as a means of measuring whether and to what extent a biological system has transitioned to its subsequent state, e.g., diseased state. As such, if one is looking for potential effectors of that transition, one may compare samples that are expected to reach that transition state both in the presence and absence of such potential effectors of that transition. In some cases, for example, pharmaceutical candidates or other interventions may be the effector in question. By comparing a system treated with such an intervention and comparing to an untreated sample, where both are reaching a transition point, one can potentially identify drug candidates that have the ability to stop or slow that transition, and potentially prevent the onset, or further progression of that transition, e.g., the disease state.

In addition to the above-described complexity that is readily analyzable using the methods described herein, one may also readily analyze a plurality of different proteins of interest (e.g., as described in greater detail below) from any given sample, simply by using affinity reagents specific for that protein of interest and its modifications. In particular, a given analysis may be able to carry out the characterization of multiple proteoforms and their relative abundances on one or more samples as described above, but on 2, 3, 4, 5, 6, 7, 8, 9, 10, 20, 50 or more different specific proteins of interest from each sample.

The exponentiation of both the complexity of biological systems, as well as the power of the methods described herein, may be exemplified with reference to the analysis of the microtubule-associated Tau protein and its proteoforms, which have been broadly implicated in the onset and progression of neurodegenerative diseases like Alzheimer's. By way of example, and with further reference to Example 6, below, Alzheimer's disease onset and progression have long been correlated with the build-up of phosphorylated forms of Tau protein as plaques in the brains of afflicted patients. However, detection methods have, to date, lacked the ability to individually characterize the patterns of phosphorylation of multiple Tau proteoforms in those patients, or understand the progression of modification of Tau protein in those patients at the onset and during the progression of the disease. Because the methods described herein utilize a single molecule detection method, one can readily characterize large numbers of proteoforms of the Tau protein, including the many proteoforms present in model systems of Alzheimer's disease as well as in clinical samples from patients afflicted with the disease, the relative abundances of those proteoforms, and comparisons of those, abundance profiles among and between multiple different samples.

For example, Tau proteoforms present in a sample may differ significantly, e.g., in patterns of phosphorylation of the Tau protein or relative abundances of one or more different proteoforms, depending upon whether the sample is derived from a healthy patient, a patient in the early stages of Alzheimer's disease or a patient with more aggressive forms of Alzheimer's disease. A set forth elsewhere herein, analysis of Tau proteoforms, e.g., patterns of phosphorylation in Tau proteins, provides further evidence that it is not merely phosphorylation, or even the extent of phosphorylation, but the order of phosphorylation that may be of significant impact in the progression of the disease.

Accordingly, with respect to the analysis and characterization of the Tau protein in samples, using the methods, processes, systems, reagents and components thereof (referred collectively herein as "platform" for ease of reference) described herein, one could potentially detect any number of the potential modifications to the Tau protein as are set forth in Table 1 or Table 2, below, as well as the various splice forms set forth in FIG. 3. Further, one may readily characterize the relative abundances of the Tau proteoforms present in any sample, and then compare those among multiple samples to identify potential progression pathways, potential interventions, or potential diagnostic indicators of disease onset or progression.

From a general perspective, and in a simple sense, one may characterize a state of progression of disease in a patient by determining the relative abundance of two or more proteoforms, such as the ratio of protein that is phosphorylated at a first location and protein that is phosphorylated at the first location and a second location, from samples that reflect different time points for a patient who is suffering, or potentially suffering from a disease like Alzheimer's. That relative abundance or ratio may be indicative of the progression of a given disease.

In the case of Tau proteoforms in Alzheimer's disease, for example, and as described in Example 5, below, phosphorylation of T181 appears to favor, or be a facilitating precondition in some cases, to subsequent phosphorylation of T217, based the relatively low occurrence of pT217 modifications in the absence of pT181 modifications. Accordingly, characterization of the relative abundance of tau proteins carrying the pT181 modification and proteins carrying both pT181 and pT217 modifications, where higher ratios of doubly modified proteoforms may indicate further progression of the disease state.

III. Reagents

As alluded to above, the present disclosure provides for the various reagents used in the herein described methods and systems. For example, included herein are affinity reagents, and combined libraries of affinity reagents that have relatively high affinity for specific characteristics of different proteoforms of a given protein of interest. These reagents may include antibodies, antibody fragments, aptamers, binding proteins, binding peptides, or the like that are capable of specifically binding to a given characteristic of a proteoform of the protein of interest. In particularly preferred aspects, the affinity reagents may include detectably labeled antibodies or binding fragments of antibodies, such as fluorescently labeled antibodies. For proteoform analysis, such libraries may include 2, 3, 4, 5, 6, 7, 8, 9, 10, 15, 20 or more different affinity reagents that have binding specificity for different characteristics of proteoforms for each different protein of interest for which proteoform analysis is desired. In some cases, the libraries may include reagents that target 1, 2, 3, 4, 5, 6, 7, 8, 9, 10, 15, 20 or more different proteins of interest and their respective proteoforms. These libraries are typically stored in multi-well plates or other similar storage vessels where each different reagent or set of reagents is separately stored from each other. In some cases, multiple different reagents may be stored within the same reagent vessel or storage component thereof, where they may be differentiated during detection, e.g., through detectably different fluorescent labels attached to the different reagents, e.g., different fluorescent labels having different emission spectra or other optical characteristics. Detectable labels may generally be coupled to affinity probes using known mechanisms, e.g., through standard chemical attachment processes, e.g., click chemistry, or through intermediate binding groups, e.g., streptavidin/biotin, SpyCatcher/SpyTag, etc.

For purposes hereof, the affinity reagents useful in performing particular analyses for proteoforms may typically include affinity reagents that bind specifically to specific forms of the protein or proteins of interest, e.g., bearing specific post translational modifications, or for regions of the protein(s) of interest that may be lacking in certain splice isoforms of the protein. Such affinity reagents may, in many cases, be acquired from commercial sources where available, e.g., Abcam PLC, or Cell Signaling Technology, Inc. Alternatively, generation of affinity reagents, e.g., antibodies, antibody fragments etc., may be generated using known techniques, including, for example polyclonal and monoclonal antibody generation methods generated against polypeptides representing the particular epitope of interest, phage display Fab generation methods, and the like.

Reagent libraries for use in analyzing Tau isoforms and proteoforms may include antibodies specific for each of the various characteristics of the Tau isoforms and proteoforms. In particular, Tau protein has been found to be expressed in a number of splice isoforms, including those that are distinguished by the number of tubulin binding domains that they include, 3 (3R) or 4 (4R), in the C-terminal of the protein and by one (1N), two (2N), or no (0N) inserts in the N-terminal domain, e.g., as described in FIGS. 3A and 3B, below. Likewise, such libraries may include affinity reagents that are specific for individual phosphorylation sites in these different Tau isoforms, including, for example, those phosphorylation sites set forth in FIG. 4, and described in greater detail below.

As a further example, the affinity reagent libraries or panels for use in analyzing Tau proteoforms may comprise a panel of a plurality of affinity reagents that are capable of differentially binding to different isoforms, or different post translational modifications of different Tau proteoforms. For example, in some cases, affinity reagent libraries or panels may comprise one or more affinity reagents (such as one or more antibodies (or binding fragments or portions thereof)) selected from affinity reagents that specifically bind to phosphorylated residues in the Tau protein as set forth in Table 1 or Table 2, below. In some cases, the affinity reagent panel may include 1, 2, 3, 4, 5 or 6 different affinity reagents that are each capable of specifically binding to a phosphorylated residue in the Tau protein selected from: pT181, pS202, pT205, pS214, pT217, and pT231 (where the designation provides the full length Tau residue number and amino acid designation). Additionally or alternatively, the panel of affinity reagents may include one or more affinity reagents specific for different regions or residues within the full-length Tau protein that may be lacking in certain isoforms. As such, affinity reagents for such isoforms may include affinity reagents that differentially target such different isoforms, such as antibodies (or binding fragments or portions thereof) which are anti-0N (binding to Tau proteins lacking both the N1 and N2 regions), anti-2N (binding to proteins possessing both the N1 and N2 region), anti-3R (binding only Tau proteins having 3 of the 4 R regions, e.g., R1, R3 and R4), anti-4R (binding to Tau proteins possessing all 4 R regions (R1-R4)), Tau13 (binding to amino acid residues 15-25 in the Tau protein).

In accordance with certain aspects of the platform described herein, the reagent libraries or panels described herein may additionally include pan-Tau affinity reagents, such as antibodies (or binding fragments or portions thereof), which are capable of binding any form of the Tau protein, regardless of its modification(s) or splice form(s), such as the Tau7 anti-Tau antibody, and/or other antibodies to the Tau protein regardless of form or modification, such as the ADx216 antibody, available from ADx Neurosciences (Ghent, Belgium). Such pan-Tau antibodies or reagents may be useful in identifying the presence and/or quantity of all forms of the Tau protein in the assay, e.g., on an array.

Figure 4:
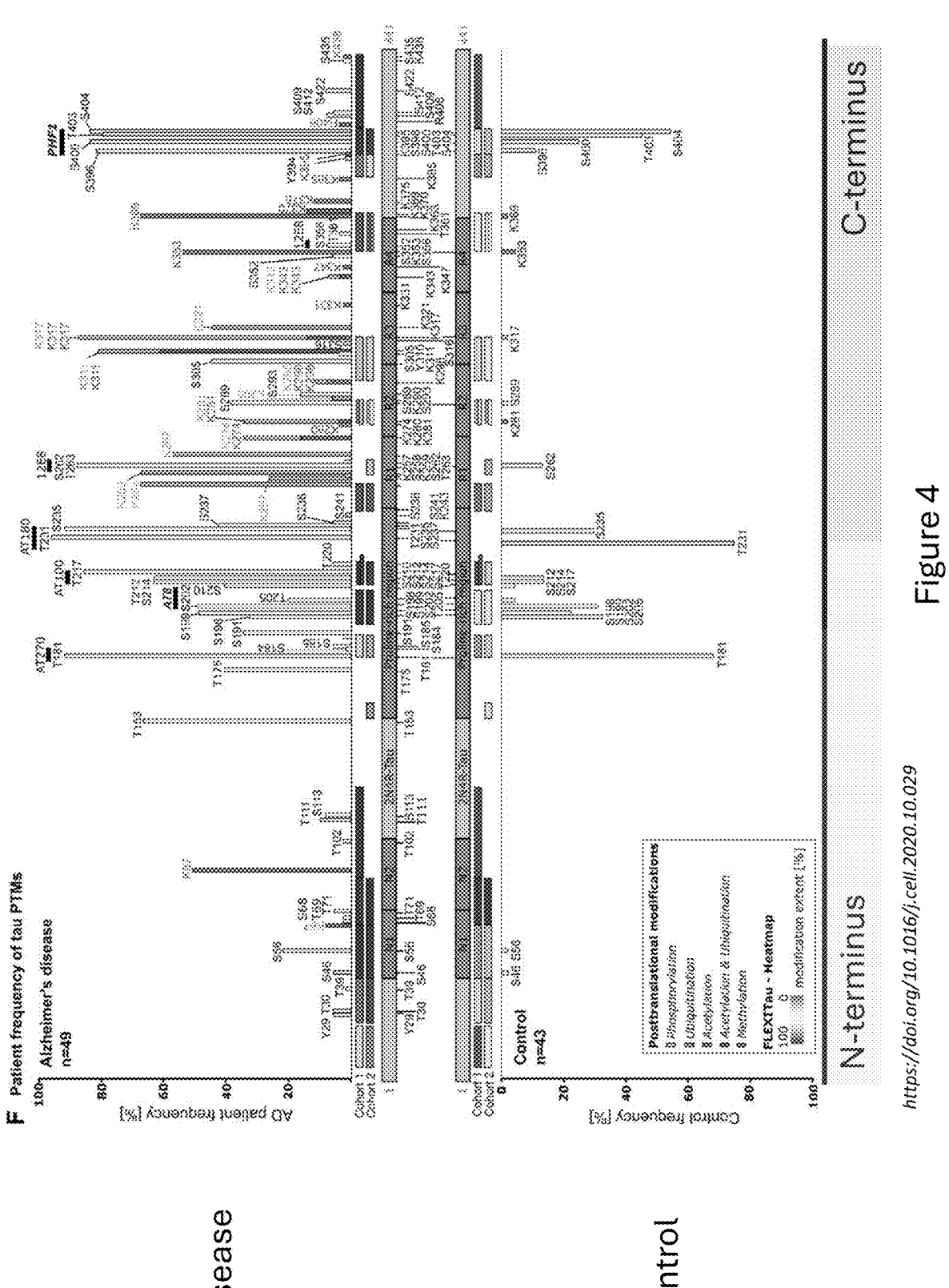
FIG. 4 shows different post translational modification sites for Tau, and a comparison of sites from control tissues and tissues from Alzheimer's patients.

In addition or alternatively to libraries or panels of affinity reagents may additionally include one or more affinity reagents that are capable of specifically binding to the additional modifications to the Tau protein that were described by Wesseling, et al., Cell 183(6):1699-1713 (Dec. 10, 2020) (the full disclosure of which is incorporated herein by reference in its entirety), as shown in FIG. 4, and as set forth in Table 1, below:

TABLE 1

| Phosphorylation | | Ubiquitylation | Acetylation | Acetyl. or Ubiq. | Methylation |
|---|---|---|---|---|---|
| pY29 | pS214 | ubK254 | acK280 | K274 | meK67 |
| pT30 | pT217 | ubK257 | acK298 | K281 | meK87 |
| pT39 | pT231 | ubK259 | acK317 | K298 | meR406 |
| pS46 | pS235 | ubK267 | acK331 | K311 | meK438 |
| pS56 | pS237 | ubK274 | acK343 | K317 | |
| pS68 | pS238 | ubK281 | acK347 | K343 | |
| pS69 | pS241 | ubK290 | acK353 | K395 | |
| pT71 | pS262 | ubK298 | acK369 | | |
| pT102 | pT263 | ubK311 | acK370 | | |
| pT111 | pS289 | ubK317 | acK375 | | |
| pS113 | pS293 | ubK321 | acK385 | | |
| pT153 | pS305 | ubK343 | | | |
| pT175 | pS316 | | | | |
| T181 | S356 | | | | |
| S184 | T361 | | | | |
| S185 | S396 | | | | |
| S191 | S400 | | | | |
| S198 | T403 | | | | |
| S199 | S404 | | | | |
| S202 | S409 | | | | |
| T205 | S412 | | | | |
| S210 | S422 | | | | |
| T212 | S435 | | | | |

In some cases, the analysis of the tau proteoforms may focus on a broader range of modifications within the tau protein. For example, in some cases, affinity reagents may be targeted at the broader range of post translational modifications for tau that are set forth in Table 2, below (i.e., affinity reagents that possess specific binding affinity for epitopes within tau that include such individual modifications) (see, e.g., phosphosite.org).

TABLE 2

| | | Phos. | | | | Meth. | Sum. | Glycos. |
|---|---|---|---|---|---|---|---|---|
| Acet. | Ubiq. | | | | | | | |
| acK491 | ubK491 | pT17 | pS235 | pY514 | pT636 | m1K44 | smK657 | glT123 |
| acK591 | ubK571 | pY18 | pS238 | pS515 | pS637 | m1K381 | | glS525 |
| acK597 | ubK598 | pY29 | pD350 | pS516 | pS641 | m3K383 | | glS555 |
| acK598 | ubK607 | pT30 | pS355 | pS519 | pS658 | m1K480 | | glS673 |
| acK615 | ubK628 | pT39 | pS369 | pT522 | pS669 | m1K497 | | glN676 |
| acK628 | ubK660 | pS46 | pS382 | pS525 | pS673 | m1K571 | | glS717 |
| acK638 | ubK670 | pT50 | pT386 | pS527 | pT678 | m1K576 | | |
| acK648 | ubK686 | pT52 | pS388 | pT529 | pT690 | meK634 | | |
| acK660 | ubK692 | pS56 | pS396 | pS531 | pT694 | m3R666 | | |
| acK664 | | pS61 | pS411 | pT534 | pT703 | | | |
| acK686 | | pT63 | pT449 | pT537 | pY711 | | | |
| acK687 | | pS64 | pS451 | pT548 | pS713 | | | |
| | | pS68 | pT466 | pS552 | pS717 | | | |
| | | pT69 | pT470 | pS554 | pT720 | | | |
| | | pT71 | pP476 | pS555 | pS721 | | | |
| | | pT95 | pQ482 | pA556 | pS726 | | | |
| | | pT101 | pT486 | pS558 | pS729 | | | |
| | | pT102 | pT492 | pT562 | pS730 | | | |
| | | pT111 | pP493 | pS575 | pT731 | | | |
| | | pS113 | pA495 | pS602 | pS733 | | | |
| | | pS171 | pT498 | pS606 | pS739 | | | |
| | | pT173 | pS501 | pS610 | pT744 | | | |
| | | pP201 | pS502 | pS622 | pS750 | | | |
| | | pS214 | PS508 | pY627 | pS752 | | | |
| | | pS232 | pS512 | pS633 | | | | |

Acet = acetylation;
ubiq = ubiquitylation;
phos = phosphorylation;
meth = methylation (me-methylation, m1-monomethylation, m2-dimethylation, m3-trimethylation);
sum = sumoylation;
glycos = glycosylation In certain aspects, the methods and affinity reagent libraries or panels described herein may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50 or more of the aforementioned affinity reagents that are capable of differentially binding to any of the different modifications to or isoforms of the Tau protein as set forth above in either of Table 1 or Table 2. In some cases, the reagent libraries or panels may include affinity reagents capable of differentially binding to different modifications or isoforms of the Tau protein, including up to 100 different affinity reagents, up to 50 different affinity reagents, up to 30 different affinity reagents, up to 25 different affinity reagents, up to 20 different affinity reagents, or up to 10 different affinity reagents In addition to the foregoing Tau characteristics, in some cases, it may be desirable to be able to characterize aggregated or multimeric forms of Tau that are present in a sample, as such multimeric forms are believed to be linked to the pathology of neurodegenerative diseases like Alzheimer's Disease. In such cases, affinity reagents that target aggregated or multimeric forms of Tau may be particularly useful in characterizing the Tau proteoforms present in a sample. The ability to specifically identify multiple Tau presences at any location on an array allows for subsequent separate evaluation of aggregated and non-aggregated forms of Tau, including potential quantitation of aggregated Tau in a sample.

While the methods, processes, systems, reagents etc. described herein may be employed to identify most if not all of the above-referenced modifications to the Tau protein described in Tables 1 and 2 above, and in turn characterize proteoforms that include those modifications, in many cases, preferred analyses will focus primarily on phosphorylation modifications, and/or ubiquitylation modifications to the Tau protein, as these have been cited as more relevant to Alzheimer's pathology. As such, in preferred aspects, a plurality of the modifications that are analyzed and detected may be phosphorylation modifications and/or ubiquitylation modifications to the Tau protein. In some cases, the analysis may detect and identify at least 2, 3, 4, 5, 6, 7, 8, 9, 10, 11, 12, 13, 14, 15, 16, 17, 18, 19, 20 or more phosphorylation modifications set forth in Table 1 or 2, above, within the Tau protein. Likewise, in some cases, the analysis may detect and identify at least 2, 3, 4, 5, 6, 7, 8, 9, 10, 11, 12, 13, 14, 15, 16, 17, 18, 19, 20 or more ubiquitylation modifications set forth in Table 1 or 2 above.

While discussed in greater detail with respect to analysis of Tau proteoforms, it will be appreciated that the platform described herein may be applicable across a range of biologically important proteins of interest and their respective proteoforms, e.g., proteoforms wherein different profiles are indicative of widely varying states of disease, health and other key biological functions. Examples of such other proteins of interest include, for example, amyloid beta, BAG3, Superoxide dismutase (SOD), and other CSF biomarkers associated with neurodegenerative diseases, such as alpha-synuclein, Aβ42, NfL, neurogranin, sTREM2, YKL-40, GFAP, IL6, S100, and the like. Additionally, other important biomarkers for which proteoform characterization is desirable include proteins like EGFR, p53, phosphatase and tensin homolog protein (PTEN), PD-L1, WEE1 nuclear kinase, retinoblastoma protein (RB), CD44, K-RAS, N-RAS, H-Ras, based upon theirs and their different forms' roles in cancer development and progression, as well as myriad other protein biomarkers, such as MeCP2, histone proteins, and the like, whose post translational modifications are implicated in a wide variety of biological process and dysfunction. As will be appreciated, affinity reagents for the foregoing proteins may generally be available from commercial sources, or readily generated using known techniques.

IV. Kits

In addition to the foregoing reagents, also provided herein are kits useful in carrying out the analyses described herein, which kits may include the affinity reagents described above, along with one or more of the enrichment reagents used to enrich for low abundance proteins and proteoforms, e.g., beads and antibodies used for the immune-isolation and/or immunoprecipitation of the proteins of interest, wash and other elution reagents, for such enrichment. Such kits may also include the flow-cells and arrays used to immobilize proteins of interest in a single molecule, optically detectable format for subsequent analysis in appropriately configured optical detection systems described below. Such kits will typically include instructions for carrying out the enrichment, flow-cell deposition, interrogation and follow on analysis of biological samples using such kits.

V. Systems

Figure 10:
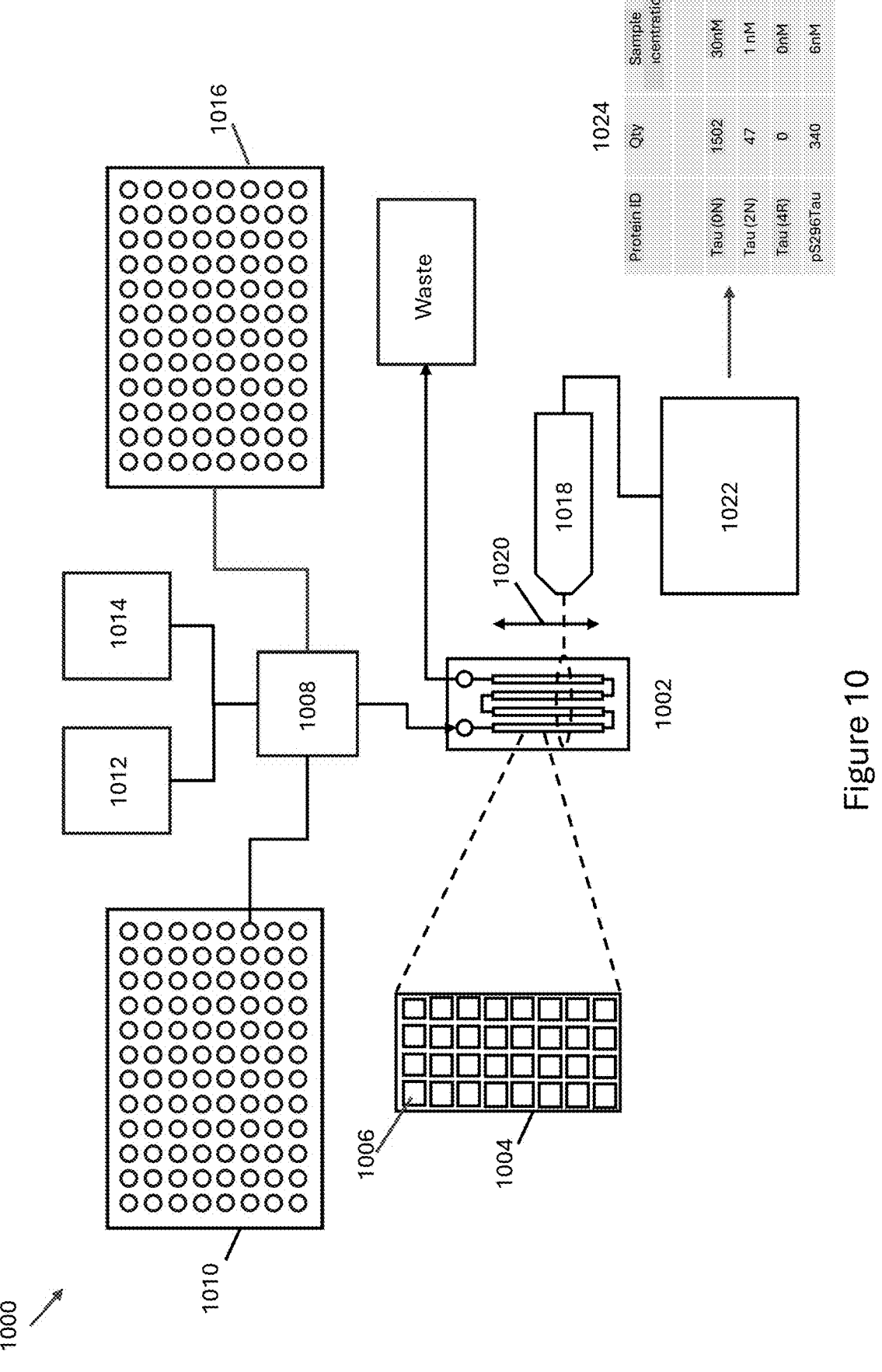

As also noted above, provided herein are systems for carrying out the analyses of different proteoforms of proteins of interest in biological samples. An example of such a system is illustrated in FIG. 10. As shown, the system 1000 includes a flowcell 1002 that includes an array surface (shown as 1004) within the channels of the flow cell upon which individual protein molecules from a sample may be deposited and immobilized in locations 1006 that are individually addressable, and in particular cases are individually optically resolvable from each other using, e.g., fluorescence microscopy or scanning techniques.

The system will also typically include a fluidic delivery system 1008 that is configured to deliver different fluids to the flow cell 1002 through a series of fluidic lines and utilizing appropriate pumps, valves and other conventional fluid controls. The fluidics system 1008 may be fluidically coupled to various sources of fluids and reagents needed to carry out the analysis on the flow cell. For example, as shown, fluidic system 1008 is fluidly coupled to a source of a plurality of reagents 1010 (shown as a 96 well plate, although any number of different reagent storage systems of varying capacity may be employed) that includes a library of multiple affinity reagents that each have affinity for different characteristics of proteoforms of one or more proteins of interest. In certain aspects, the reagent sources include reagent libraries or panels that are fluidically coupled to the fluidic system 1008 may include a panel of antibodies that specifically recognize and bind to a particular protein or proteins of interest, including for example, the affinity reagents described above for analyzing Tau proteoforms. In certain particularly preferred aspects, the systems described herein may include reagent panels that are fluidically coupled to the fluidic system, and in many cases, thereby coupled to the flow cells described above, that include at least 2, at least 3, at least 4, at least 5, at least 6, at least 7, at least 8, at least 9, at least 10, at least 11, at least 12 or more of the aforementioned affinity reagents that are capable of differentially binding to different modifications to or isoforms of the Tau protein. In some cases, the reagent libraries or panels may include affinity reagents capable of differentially binding to different modifications or isoforms of the Tau protein, including up to 100 different affinity reagents, up to 50 different affinity reagents, up to 30 different affinity reagents, up to 25 different affinity reagents, up to 20 different affinity reagents, or up to 10 different affinity reagents.

The fluidic system 1008 may also be coupled to sources of washing fluids or buffers 1012, and removal reagents 1014 (for removing bound affinity reagents following detection), as well as any other ancillary fluids and reagents needed for the analysis. Similarly, where flow cells are prepared on the system, the fluidic system may be coupled to sources of different sample materials that are to be analyzed 1016 (again, shown as a 96 well plate, although again, any suitable sample storage system or capacity may be suitable).

The reagents sources are typically fluidly connected to the flow-cell using fluidics systems that can separately access different reagents, sample materials and other fluids, and control the timing and volume of different reagents delivered to the flow-cell at different times in order to carry out the deposition, interrogation, washing and removal steps of the analysis process. Such fluidic systems will typically include requisite valves and pumps for carrying out such fluid deliveries and include, for example, those as described in, for example, U.S. Patent Application No. WO 2023/122589A2, the full disclosure of which is hereby incorporated herein by reference in its entirety for all purposes.

The systems described herein also typically includes a detection system, such as optical detection system 1018, for detecting and recording fluorescent signals arising from different positions on the array surface. Such detection systems may generally include line scanning confocal fluorescent microscope systems, which are capable of scanning across large array surfaces (as shown by arrow 1020) to detect and record fluorescence across such surfaces at reasonably high scan rates.

The overall systems also typically include one or more computers or processors 1022 for controlling the operation of the instrument system including the fluidic system 1008 (e.g., to sample different sample sources 1016, reagent sources 1010 and delivery timing and volume of each), and detection system 1018, among other functions, and for recording the detected signals received from the detection system 1018, e.g. fluorescent signals, and analyzing such signals to identify potential binding by each of the different affinity reagents. Included in such processors 1022 may be bioinformatic software or firmware that evaluates the signals received and based upon appropriate modeling, identifies likely positive binding events, and then subsequently provides an overall assessment of which proteoforms are present at any given location on the array as well as the relative abundance of each different proteoform across the array and ultimately, within the sample being analyzed, e.g., as shown at 1024. Examples of bioinformatic software processes for analyzing such proteoform and proteome data have been described in, for example, U.S. Pat. Nos. 11,545,234, 10,473,654B1, and Eggertson, et al., bioRxiv, U.S. Patent Application No. 2022/0236282, International Patent Application Nos. PCT/US24/15132, and WO 2023/038859. Alternatively, in some cases, recorded data from the binding events, stored as digital information, digital image files, or compressed versions of such image files, may be transmitted to separate servers or cloud-based systems, which house the informatics software that performs this latter analysis and reporting.

VI. EXAMPLES

Example 1: Exemplary Proteoform Analysis Process

The following provides an exemplary process for the analysis of Tau proteoforms in biological samples.

A. Tau Protein Enrichment and Nanoparticle Attachment:

Tau proteins were immunoprecipitated from their respective samples using antibody-coated beads, by immobilizing different Tau antibodies (having specificity for the N-terminal, middle portion and C-terminal of the Tau protein sequence) on the surface of Dynabeads, and mixing the beads together in a roughly equal molar ratio. The anti-Tau coated beads were then contacted with the samples to allow binding, and then washed to remove unbound proteins. Following washing steps, the Tau proteins were then treated with methyltetrazine-PEG4-STP (4-sulfo-2,3,5,6-tetrafluorophenyl ester) (mTz) to provide a linkage group for nanoparticle attachment. The bead-bound proteins were then contacted with a molar excess of DNA origami nanoparticles including a single trans-cyclooctene group (TCO) overnight to allow conjugation. Following conjugation, nanoparticle-coupled Tau proteins were then competitively eluted using short epitope peptides representing the binding epitopes for the three antibodies used in the immunoprecipitation. Similar conjugation techniques are employed in preparing standard and control polypeptides except without the need for immunoprecipitation.

Flow-Cell Preparation and Loading: Flow cells included a silicon base layer having nanoscale features (sized to allow coupling of the origami nanostructures) patterned into a resist layer where the base of the features includes a silane derivatization coupled to NHS ester-PEG-azide functional groups which were then coupled to attachment oligonucleotides.

B. Antibody Preparation

Fluorescently labeled DNA nanoparticles containing one or more streptavidin groups are incubated with 2 molar equivalents of each type of biotinylated anti-Tau antibody with equivalents calculated relative to the measured number of Streptavidin attached per nanoparticle. The antibody conjugated nanoparticles are purified from excess unconjugated antibody via HPLC-Size Exclusion Chromatography (SEC). Fractions corresponding to the nanoparticle peak are pooled and concentrated using spin filtration to provide purified antibody-nanoparticle conjugates.

C. Detection

Protein analysis was carried out on an instrument system that included integrated fluid handling and optical detection for analysis of the flow cell. Prepared flow cells are placed upon a mounting stage in the instrument and coupled to the integrated fluidic system that is configured to deliver reagents from multiple reagent sources, as well as buffers and wash solutions to and through the flow cell. The mounting stage also positions the flowcell such that its functionalized surface is exposed to and scannable by an optical fluorescence detection system, such as a scanning fluorescent laser microscope system, also integrated into the instrument.

The flow-cell is first primed by passing running buffer through the flowcell. This is followed by injection of nanoparticle-conjugated Tau proteins, where deposition onto the flow cell surface was mediated by the annealing of complementary oligonucleotides between the nanoparticle and pre-immobilized surface oligonucleotides on the flow cell surface. The resulting Tau protein array surface was then washed with running buffer to remove any unbound proteins and nanoparticles.

The Tau protein arrays were then iteratively interrogated with the relevant probes under appropriate binding conditions, and washed to remove unbound material. The interrogated arrays were then scanned using the optical detection system and images of fluorescent signals from the array, indicating antibody binding at the location from which the signal was detected, were captured. Cycles were repeated with different probes as well as with duplicate interrogations (multiple probings with the same probe).

D. Analysis

Analysis images were processed as previously described in Aksel et al. Briefly, patterned array and single pad boundaries were determined using subarray fluorescent patterns excited by the 488 nm laser. The mapping between 488 nm and 647 nm laser acquired images uses subarray locations in the 488 nm scan and fiducial beads in the 647 nm scans. A calibration flow-cell is used to allow mapping of locations directly from 488 nm images to 647 nm images. A reference base scan is taken for both the 488 nm and 647 nm images. The 647 nm-reference scan is used to align all subsequent 647 nm images. Each image was normalized against the background. Background intensity estimates were calculated by tiling the image and computing the $5^{th}$ percentile for each tile. Then, the tiles are used to solve for a 2-dimensional paraboloid. The image is then normalized against this smooth paraboloid. The primary feature score was computed for each candidate object by summing the logarithm of 5 pixels forming a 3×3 t-shape centered on each landing pad in the background normalized image.

E. Proteoform Analysis

The proteoform decoding algorithm analyzes a series of fluorescent signals as antibody binding measurements acquired on a sample with unknown proteoforms and determines the abundance of each epitope in the sample. The decoding algorithm uses an expectation-maximization approach to estimate the probability of each proteoform in the sample. The inputs to this algorithm are the series of antibody binding measurements and the rates at which the antibodies bind to their target epitopes. The model employs a Poisson binomial distribution, where the likelihood that the proteoform contains a given epitope is determined by the antibody binding rates. The output of the model is partial counts corresponding to the probability that each candidate proteoform produced the observed series of binding measurements. The number of candidate proteoforms is $2^m$, where m represents the number of antibodies used in the experiment. To account for sample-to-sample and run-to-run variation, the algorithm also estimates the binding rates for each antibody within each sample. We use control proteoforms to determine the affinity of labeled antibody binding in the presence and absence of the target epitope, and set a prior on antibody binding rates based on these control proteoforms. A uniform prior is set on proteoform abundance estimates. To account for potential protein degradation during sample prep, we discard any landing pads that do not contain at least one positive binding measurement for an antibody that targets the N-terminal region of Tau and at least one positive binding measurement for an antibody that targets the C-terminal region of Tau. This ensures that we analyze landing pads that contain full length Tau.

Example 2—Proteoform Analysis of Microtubule Associated Protein Tau

The microtubule-associated protein tau (or "Tau") forms a group of six highly soluble protein isoforms produced by the alternative splicing from the gene MAPT. The Tau protein helps stabilize the internal skeleton of neurons in the brain, and has a tube-like structure through which nutrients and other essential chemicals travel to reach different parts of the neurons. Tau is most abundant in axons is the cerebral cortex. It is less common elsewhere but is also expressed at very low levels in other neuronal cell types, such as astrocytes and oligodendrocytes. Tau has multiple functions in different locations inside and outside of neurons. It is important in a diverse range of molecular pathways including cell signaling, synaptic plasticity, and regulation of genomic stability. Tau is highly post-translationally modified, which is pivotal in defining and modulating tau localization and its roles in health and disease. In particular, hyper-phosphorylated forms of Tau have been implicated in the pathology and disease progression of Alzheimer's Disease.

Figure 3A:
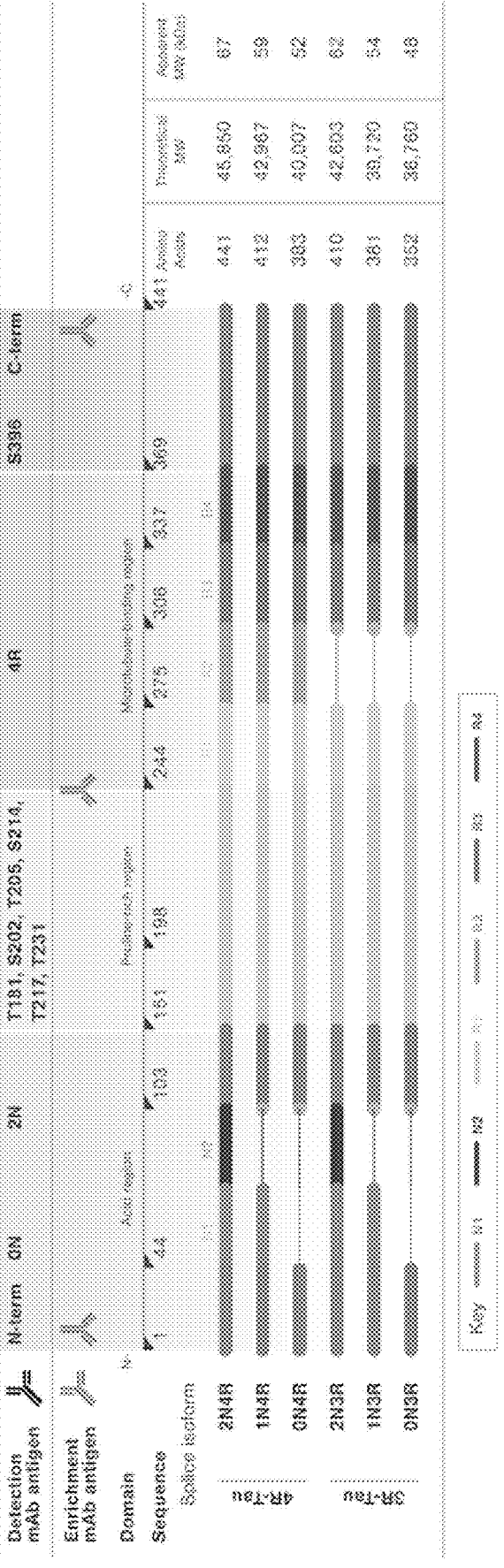
FIGS. 3A and 3B illustrate different proteoforms and isoforms of the microtubule associated protein Tau, and their relevance in biological functions.
Figure 3B:
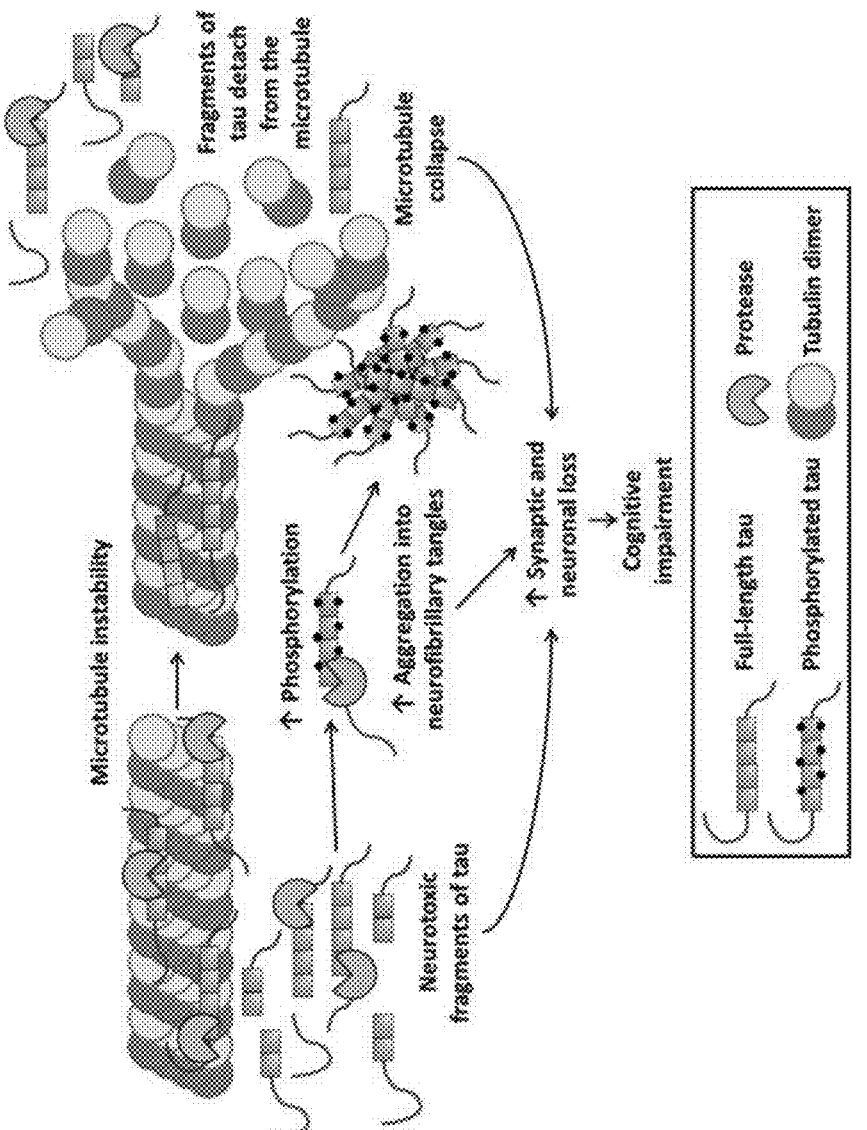

FIGS. 3A and 3B illustrate the significance of biologically relevant isoforms and proteoforms in terms of structure, function, and distribution is the microtubular associated protein Tau (MAPT). FIG. 3A shows the different Tau isoforms generated through the tau MAPT gene expression, alternative RNA splicing and protein translation which are detectable in an adult human brain. N1 and N2 tau isoforms are generated by alternate splicing of exon 2 and 3 and alternate splicing of exon 10 produces the 3R and 4R isoforms. It has further been established from post-mortem human brain studies that the 1N isoform is predominantly found in the soluble fraction of the brain. In Alzheimer's patients, the 4R isoform is highly enriched compared to healthy brain tissue. The 0N and 1N isoforms exist at higher levels in the insoluble fraction (with 0N being higher than 1N) in the brains of Alzheimer's patients. The 0N and 4R isoforms have been found to be more prone to aggregation in Alzheimer's patients. FIG. 3A also illustrates approximate epitope positions for isoform and proteoform specific detection antibodies to probe the molecular heterogeneity used for analysis of certain proteoforms and approximate epitope binding sites for antibodies used for enrichment.

FIG. 3B schematically illustrates the different isoforms of Tau that can be found as either soluble or insoluble fractions with different Tau isoforms enriched in those fractions, including, e.g., pathological insoluble fraction (fibrils) in brain, (visible by tau PET), soluble Tau fraction in brain with different isoform distribution than in fibrils, soluble Tau in CSF truncated as N-terminal fragment, and soluble Tau in plasma similar in composition to that found in CSF.

It has also been reported that highly modified proteoforms of Tau can form pathological tangles that ultimately lead to Alzheimer's Disease. This is illustrated in FIG. 4 which illustrates the different Tau post translational modifications that have been detected and their relative prevalence in both healthy and diseased brain tissue. However, conventional analysis techniques are less than ideal for identifying how those PTMs are distributed across the Tau proteome, and the specific proteoforms that are present in diseased vs. healthy tissue.

The methods and systems described herein were employed to characterize different Tau proteoforms in model systems. In each case, polypeptides or proteins to be analyzed were coupled to structured nucleic acid particles (or SNAPs) that comprised a DNA origami framework with a single point of attachment for the protein or polypeptide. These structures were then deposited on a surface of a patterned flow-cell, such that individual protein/SNAP structures would be separate and optically resolvable from each other deposited protein/SNAP structure. The flow cells were then placed into an instrument that would iteratively deliver different fluorescently labeled affinity reagents, e.g., antibodies, specific for different characteristics of the various different isoforms and proteoforms of the Tau protein, e.g., different splice versions, different phosphorylation sites, etc., with intervening wash cycles and fluorescent detection cycles to identify where on the array the various affinity reagents would bind.

Binding patterns at each site for the different affinity reagents were then analyzed to identify which characteristic of each isoform or proteoform was present at each site where a protein or polypeptide of interest was located on the array surface within the flow cell.

Figure 5:
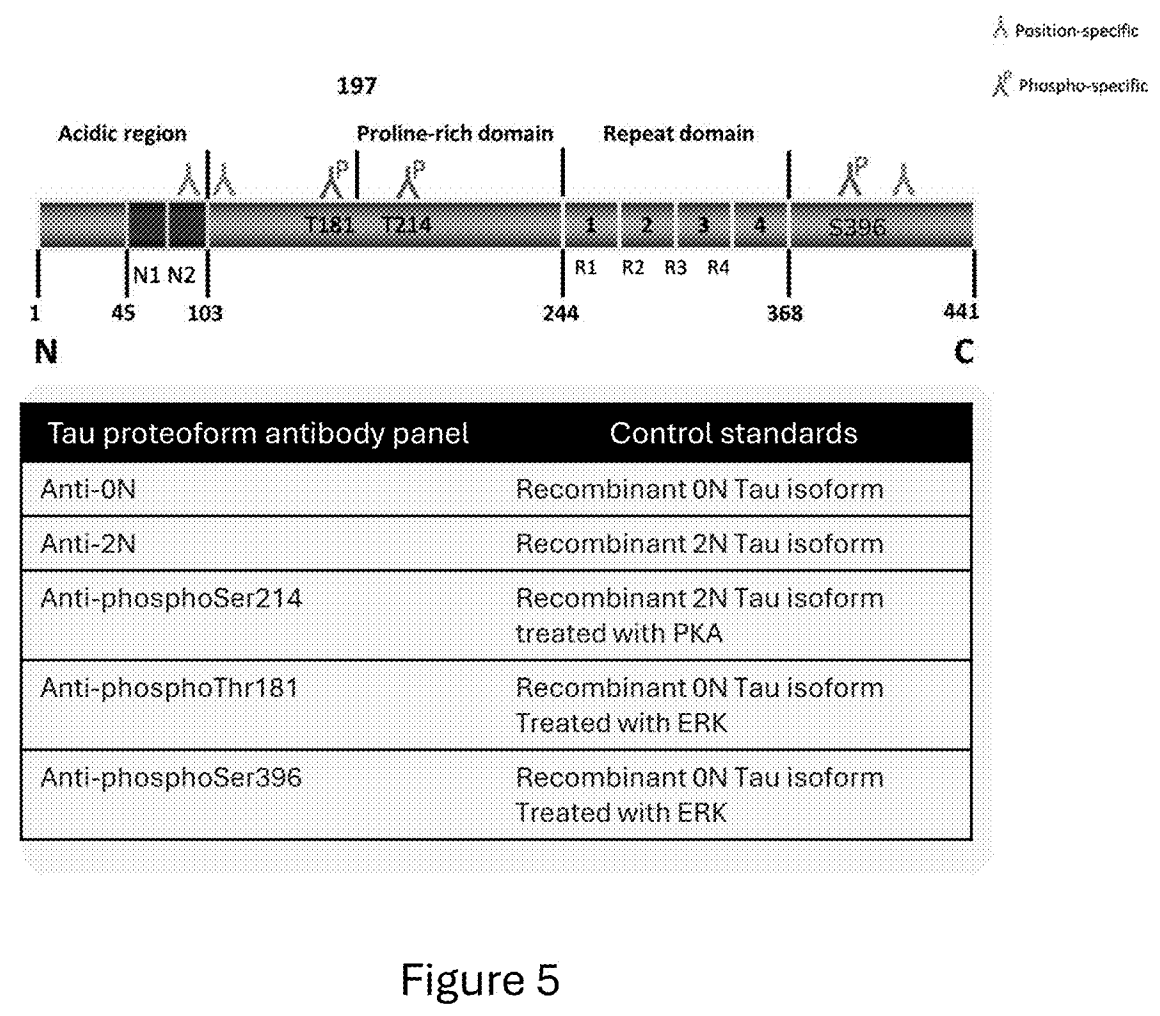

In a first experiment, a number of polypeptides were synthesized that represent specific epitopes of the Tau protein that are present and/or modified in different isoforms and proteoforms of Tau, along with two recombinant isoforms of Tau representing two different splice isoforms of the protein (0N and 2N). These peptides were loaded into a flowcell as described above and serially interrogated with fluorescently labeled antibodies that are highly specific to those epitopes. A set of antibodies was then selected to probe the molecular heterogeneity of Tau as shown in FIG. 5.

Recombinant Tau protein was used to create unmodified and phosphorylated control standards. Standards were characterized by LCMS to determine site specific modifications. These standard polypeptides were then immobilized within the flow cell and analyzed using the different corresponding detection antibodies.

Figure 6:
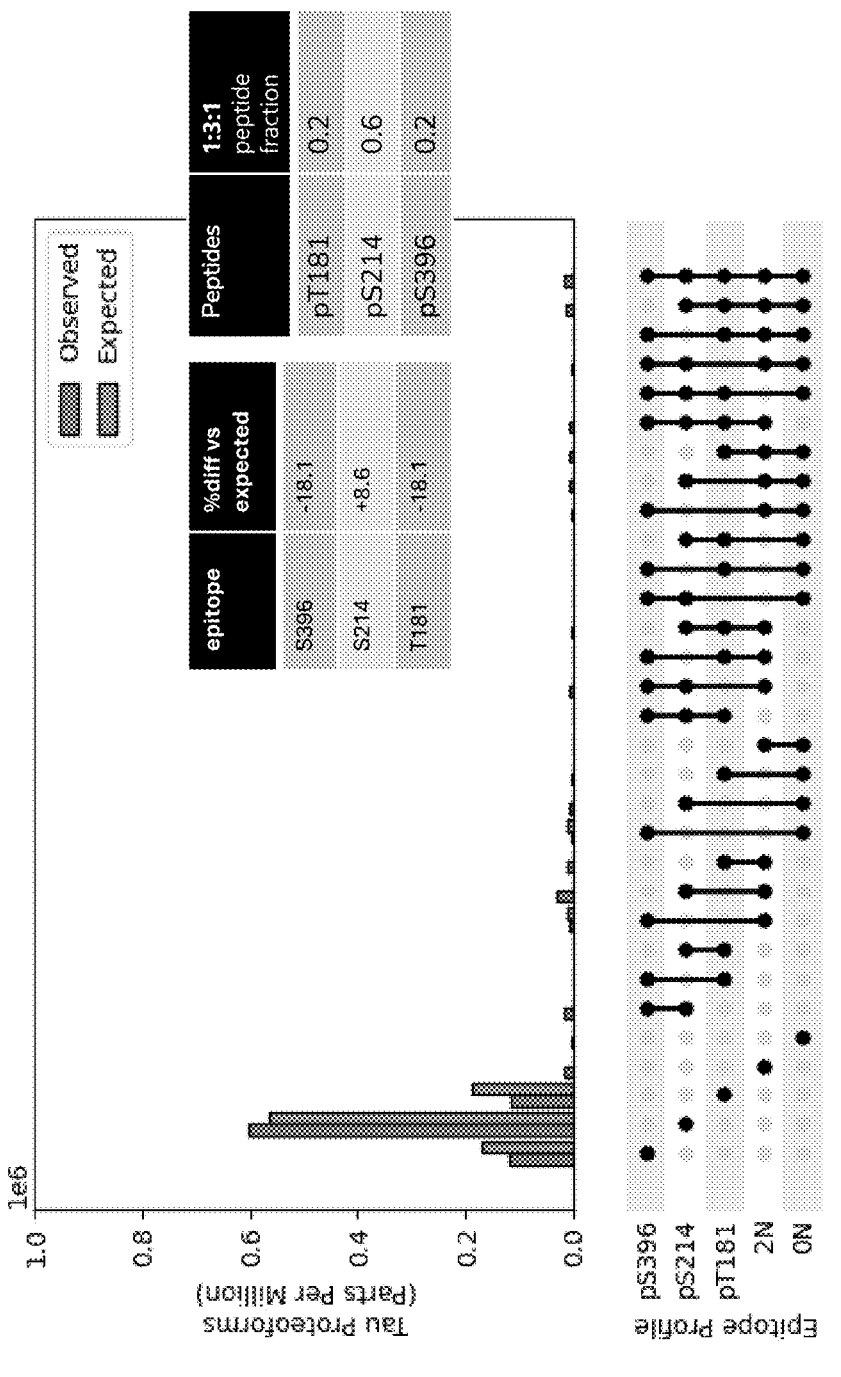
FIG. 6 shows detection of different peptides representing different post translational modifications found in Tau.

As shown in FIG. 6, probing the immobilized polypeptides with antibodies specific for three epitopes (T181, S214, S396) yielded detection of the specific polypeptide representing that phosphorylated epitope at the single molecule level on the flow-cell. In fact, not only are the epitopes detected with minimal background and false positives (signal at the bottom of the bar graph), but the relative quantities of those epitopes were also determined. In particular, a mixture of these epitopes 02.:0.6:0.2 was accurately detected with a deviation of the measured to the theoretical ratios between 9 and 18%. (see table insert in the graphics). Separately, quantitation experiments using mixtures of known but differing amounts of different Tau proteins and proteoforms show high correlation ($R^2$ of 0.9835) between expected and detected amounts.

Figure 7:
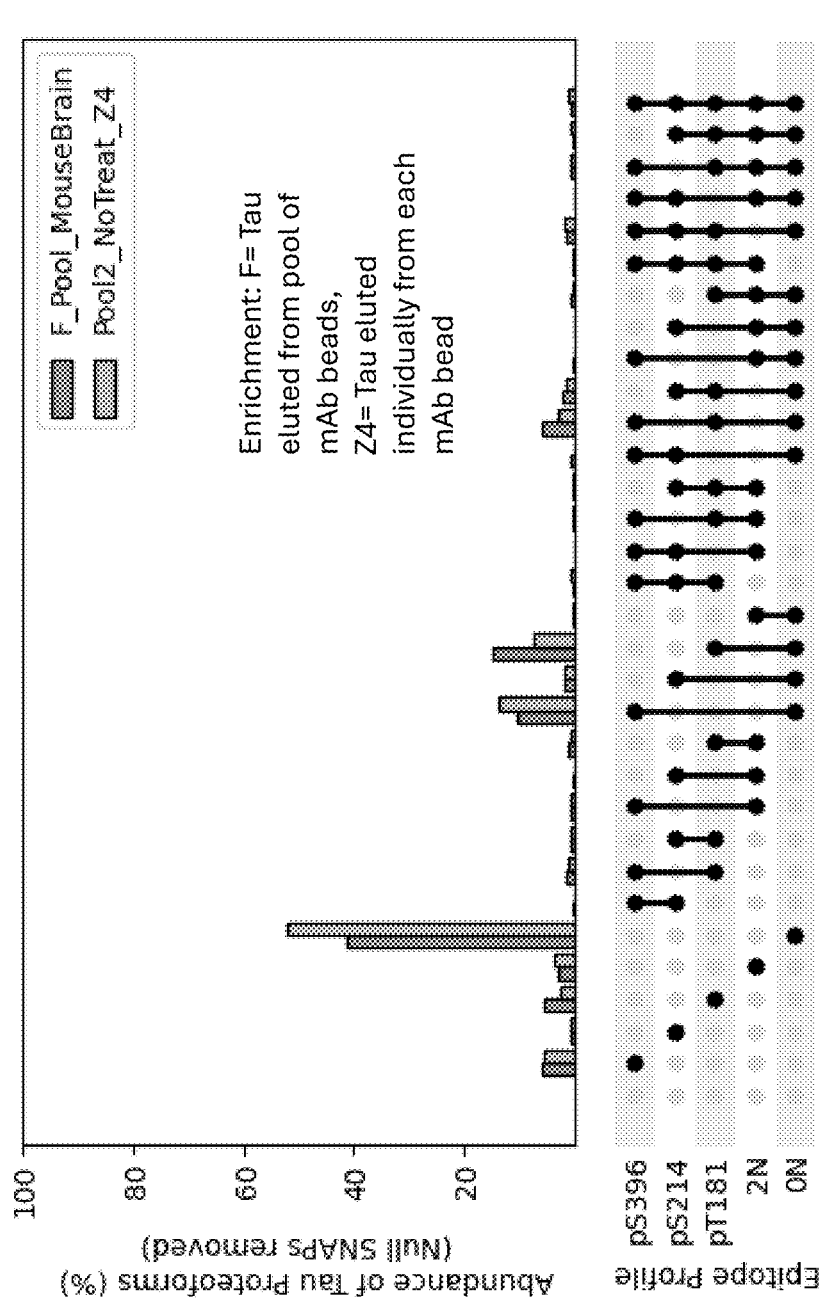
FIG. 7 shows detection and quantitation of different Tau proteoforms in humanized mouse brain models using varied enrichment schemes.
Figure 8:
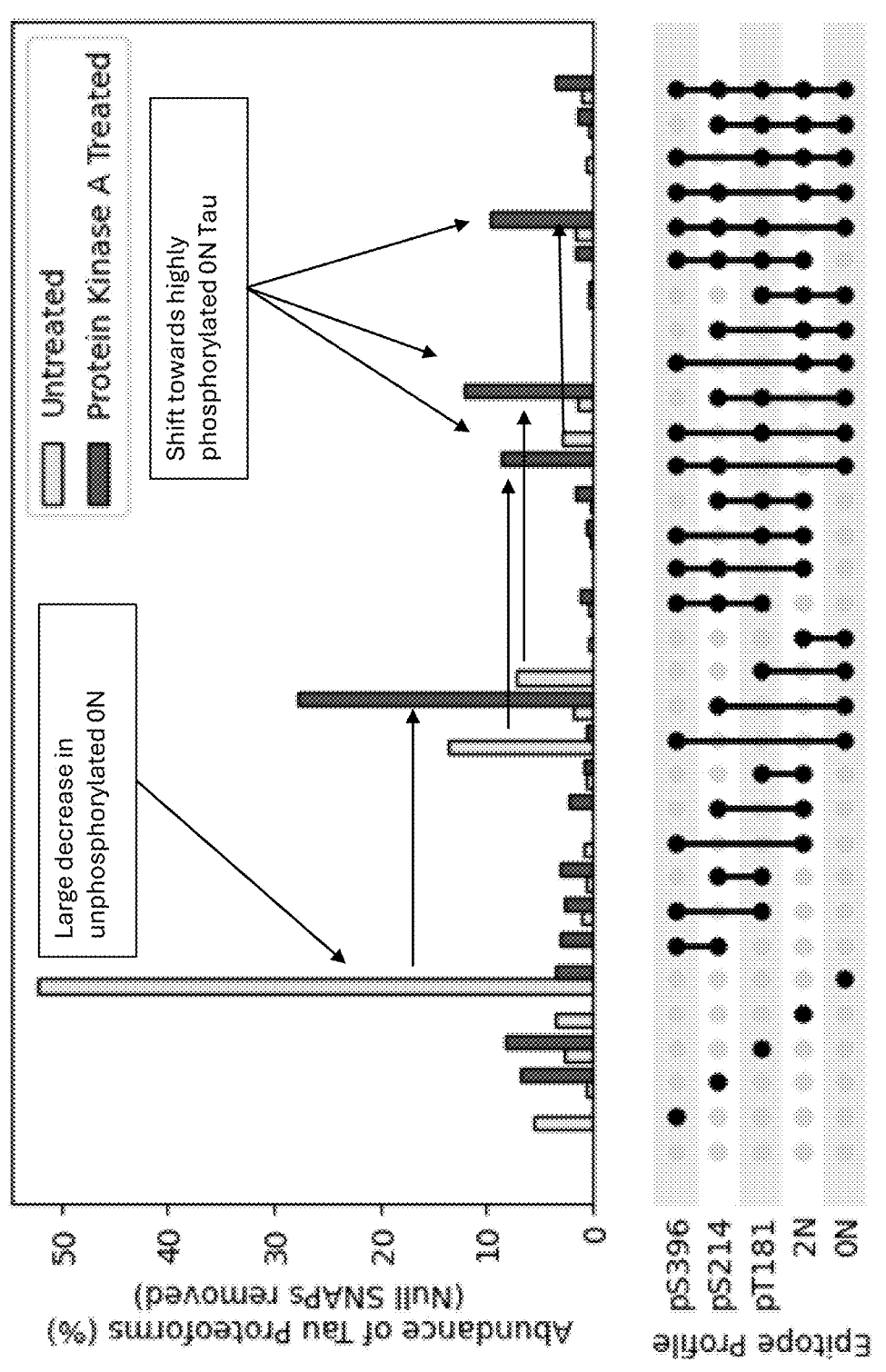
FIG. 8 shows the detected effects of Protein Kinase A treatment on tau proteins.
Figure 9:
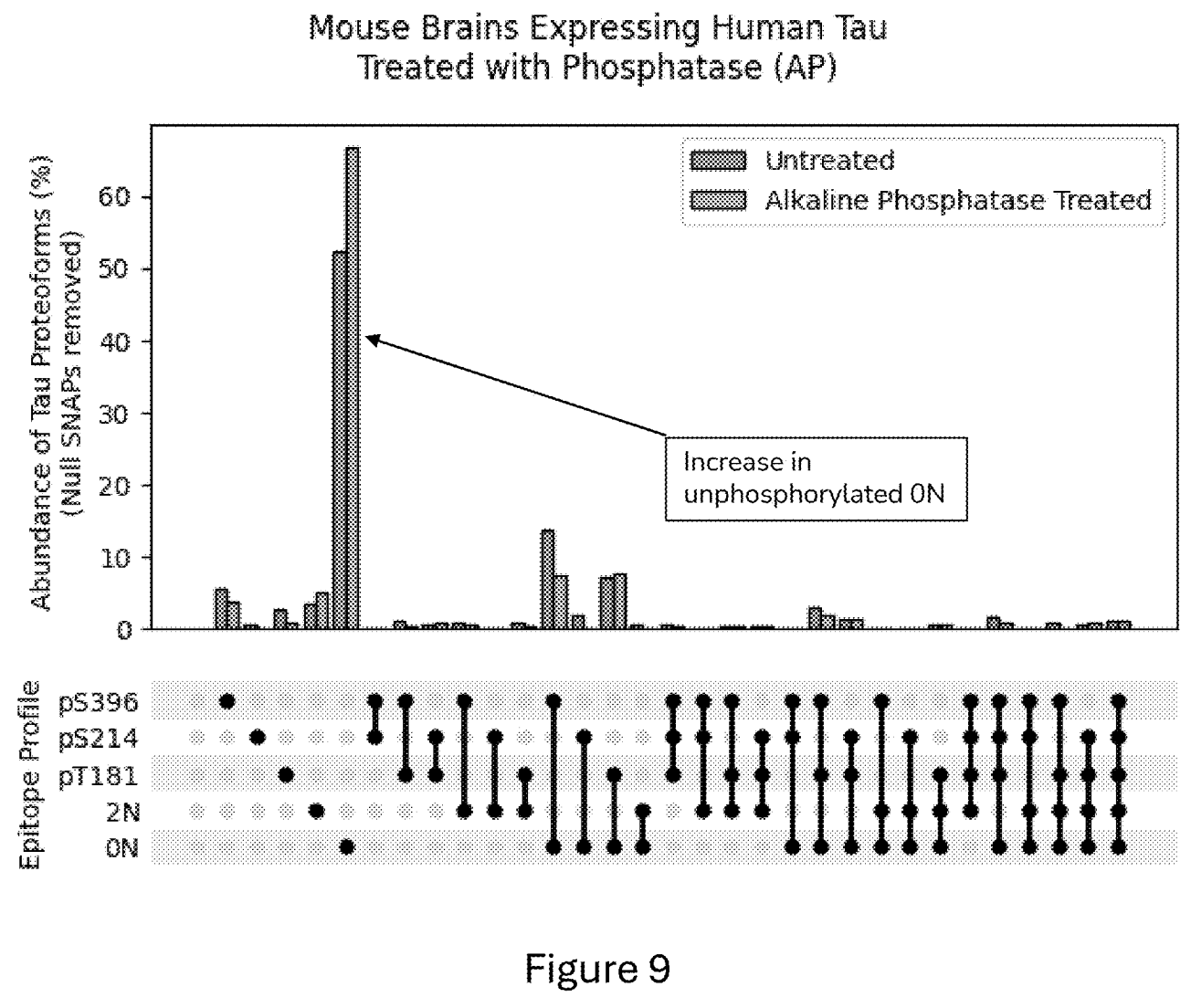

In a subsequent experiment, tissue lysates from mouse models that express human Tau in brain tissues were analyzed for the presence of different Tau proteoforms. With reference to the structures and antibodies set forth in FIG. 3, FIG. 7 illustrates the detection and relative quantitation of a variety of different Tau proteoforms enriched from those tissues using a mixture of Tau antibodies (Semorinemab and Bepranemab antibodies (available from MedChem Express, Inc.) and Tau 7 antibodies (available from EMD Millipore, Inc.)) to ensure pull down of the various different isoforms of Tau. Replicates at each site represent enrichment using a mixture of different beads where either a cocktail of antibodies was conjugated to a set of beads (Pool2) versus the separate enrichment antibodies being separately conjugated to their own beads prior to combining those beads for use (F Pool). Both enrichment cases show similar results that include showing greater abundance of the shorter, immature 0N proteoform as compared to the longer, mature 2N proteoform. In addition, several phosphorylated proteoforms of Tau were also detected in those lysates. In order to demonstrate the ability to accurately detect different phosphorylation patterns, the Tau proteins enriched from the mouse brain lysates were treated with protein kinase A ("PKA") which preferentially phosphorylates serine 214. As shown in FIG. 8, PKA treatment yields a significant shift of Tau from the unphosphorylated form to the ps214 proteoform. Conversely, as shown in FIG. 9, treatment with alkaline phosphatase results in a decrease in phosphorylated Tau proteoforms and a concurrent increase in unphosphorylated Tau.

Example 3—Quantitative Assessment of Tau
Proteoform Changes in iPSC-Derived Neurons
During Differentiation As discussed earlier, Alzheimer's disease and related neurodegenerative diseases, such as primary Tauopathies, are a significant burden in healthcare due to growing prevalence. One central element in these diseases, particularly in tauopathies, is the microtubule-associated protein, Tau. There are six major isoforms generated in the mature human brain by alternative mRNA splicing of exons 2 and 3 (either 0N, 1N, or 2N isoforms) and exon 10 (3R or 4R isoforms). Specific post-translational modifications of tau have been associated with Alzheimer's disease and other Tauopathies. However, it remains unclear which tau proteoform(s) contribute(s) most to neural dysfunction and neurodegeneration, and how. Current methods of protein analysis do not adequately address the molecular diversity of Tau proteoforms in neuronal tissue. Human-induced pluripotent stem cells (iPSC) derived from patients can be differentiated into disease-relevant neurons, providing a platform for in vitro modeling, including for the study of the pathological features of neurodegenerative disease. However, as disclosed herein, a single-molecule detection technology can allow for characterization (e.g., highly sensitive and precise identification) of Tau proteoforms to reveal Tau protein heterogeneity in iPSC-derived neurons.

FIG. 11 shows information on different organoid samples used as differing model systems in analyses herein. The techniques described herein include applying a single-molecule Tau proteoform assay to the iPSC-derived organoid models from patients containing abnormal forms of Tau from whom detailed neurological, neuroimaging, and neuropathological data are available, including Tau associated pathologies depicted in FIG. 11. An organoid model is selected with a MAPT mutation (V337M) that increases the propensity for the tau protein to aggregate. A second organoid model contains a MAPT mutation (IVS10+16) that alters MAPT splicing and results in increased levels of exon 10-containing mRNA (4R). These were then analyzed using the methods described herein, to provide a comparison of Tau proteoforms from organoids at three- and six-months of maturity between the iPSC lines of the donor genotype and their isogenic controls that underwent CRISPR/Cas9 editing to reflect the wild type, as discussed with reference to FIGS. 14 and 15, below.

A bead-based enrichment method compatible with a single-molecule library preparation was used to enrich Tau from the iPSC lines. Tau proteins were enriched using a combination of three different anti-Tau antibodies coupled to magnetic beads. The enriched proteins were then conjugated to nanoparticles before being deposited into a flow cell.

Then, in each flow cell, the first lane is used to deposit unconjugated nanoparticles that serve as a control lane (null lane) and assess non-specific binding of detection antibodies to the flow cell surface. In a second control lane (standard reference) the system deposits nanoparticles conjugated to a well-characterized, full length protein standard that is used to assess the binding frequency of epitope specific antibodies to the positive control standard. By assessing the binding patterns of detection antibodies to the full-length protein standard in the control lane and to the null lane, the system can assess the differential binding affinity and binding specificity between null and control lane, eliminating the portion of signal detected on the single-molecule system associated with non-specific binding to non-protein surfaces. In the remaining lanes of the flow cell, sample proteins conjugated to the nanoparticles are deposited for proteoform identification and quantification.

Figure 12:
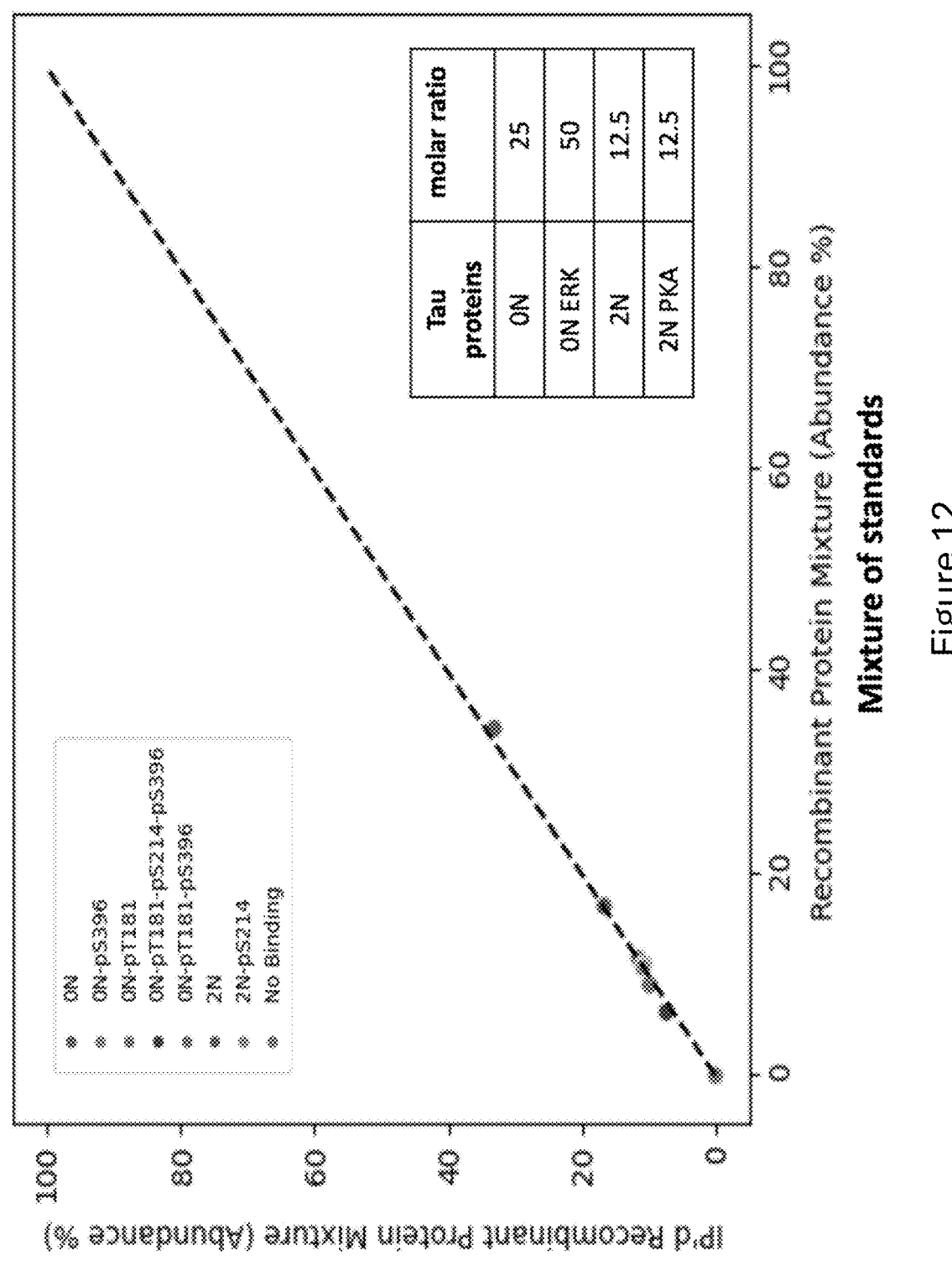
FIG. 12 shows a comparison of Tau proteoforms with a mixture of standards.

For an assay for single-molecule detection of Tau proteoforms, a mixture of Tau protein reference standards that were characterized by LC/MS and included recombinant, full-length proteins for 2N4R and 0N4R, and 2N4R treated with Phosphokinase A (2N4R-PKA) with phosphorylation at site S214 and 0N4R treated with mitogen-activated map kinase 1 (0N4R-ERK 2) phosphorylated at T181 and S396 were used. The quality of the proteoform assay was assessed, including the enrichment step by mixing the full-length Tau protein standards at a ratio as indicated in the table of FIG. 12. The Tau protein mixture was then spiked into K562 cell lysate, enriched and analyzed on the system. The ratios of Tau standards in the enriched sample were then compared to the ratios of the original mixture. The result was reproduced for two different sample mixtures.

FIG. 12 shows a comparison of Tau proteoforms with a mixture of standards. Comparing the ratio of Tau proteoforms from the mixture of standards with the enriched sample, we observe a close correlation between both sample types. No bias between the enriched sample and the original mixture was observed. The relative abundance of proteoforms in the mixture was also maintained.

Figure 13:
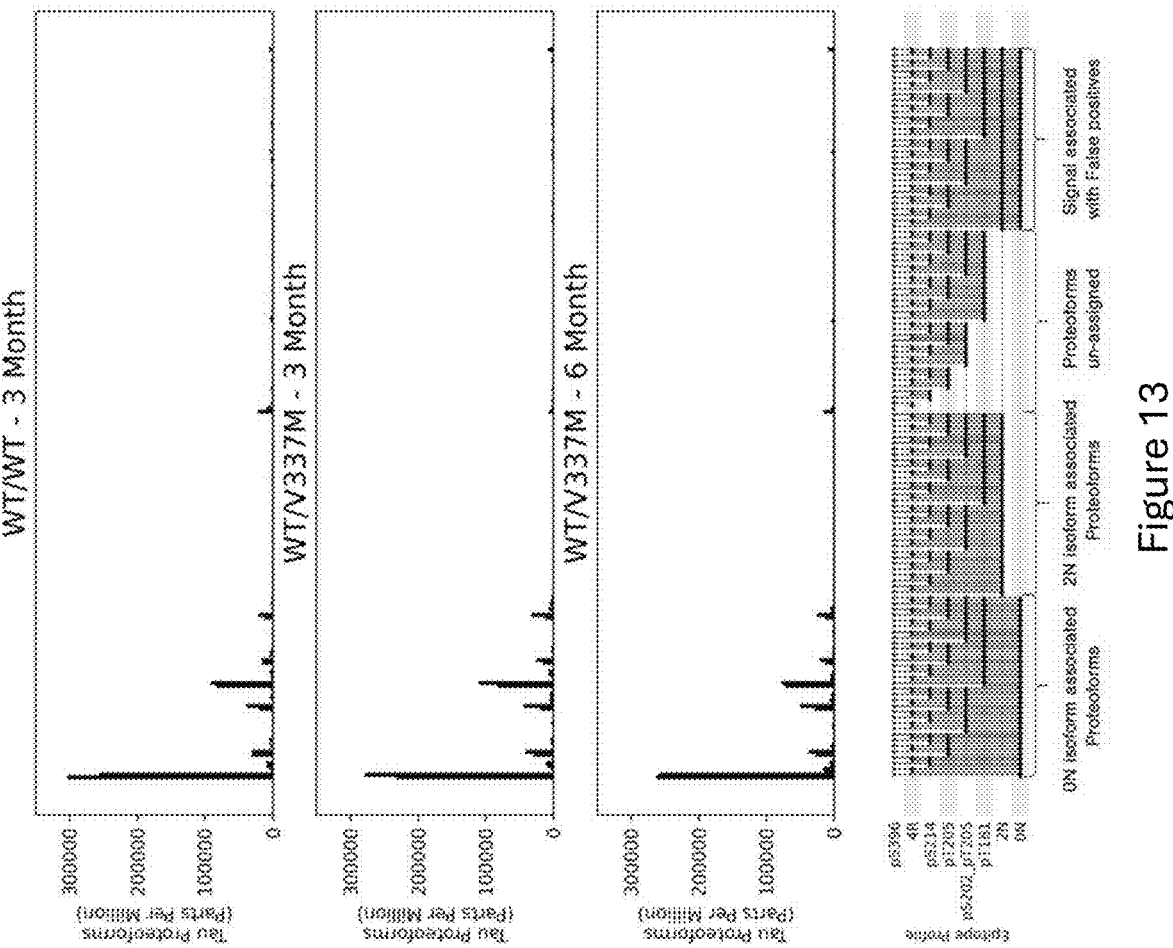
FIG. 13 shows a Tau proteoform landscape in a patient-derived iPSC organoid model during differentiation.

Example 4—Analysis of Tau Landscapes in
Different Model and Patient Derived Systems FIG. 13 shows a Tau proteoform landscape in a patient-derived iPSC organoid model during differentiation. The techniques described herein are used to enrich Tau fractions from iPSC-derived organoids comparing WT/WT with WT/V337M mutant. The V337M mutation promotes Tau hyperphosphorylation and aggregation within a human brain. In particular, FIG. 13 shows the Tau proteoforms from WT/WT, WT/V337M at three and six months maturity using eight site-specific antibodies (0N, 2N, 4R, pT181, pS202, pT205/S207, pS214, pS396) with the potential to assess 256 epitope combinations. This shows a complex landscape of mostly 0N isoform-associated Tau proteoforms in those organoids, revealing molecular heterogeneity in a model of neurodegenerative disease that is largely undefined by other proteomic techniques.

Figure 14:
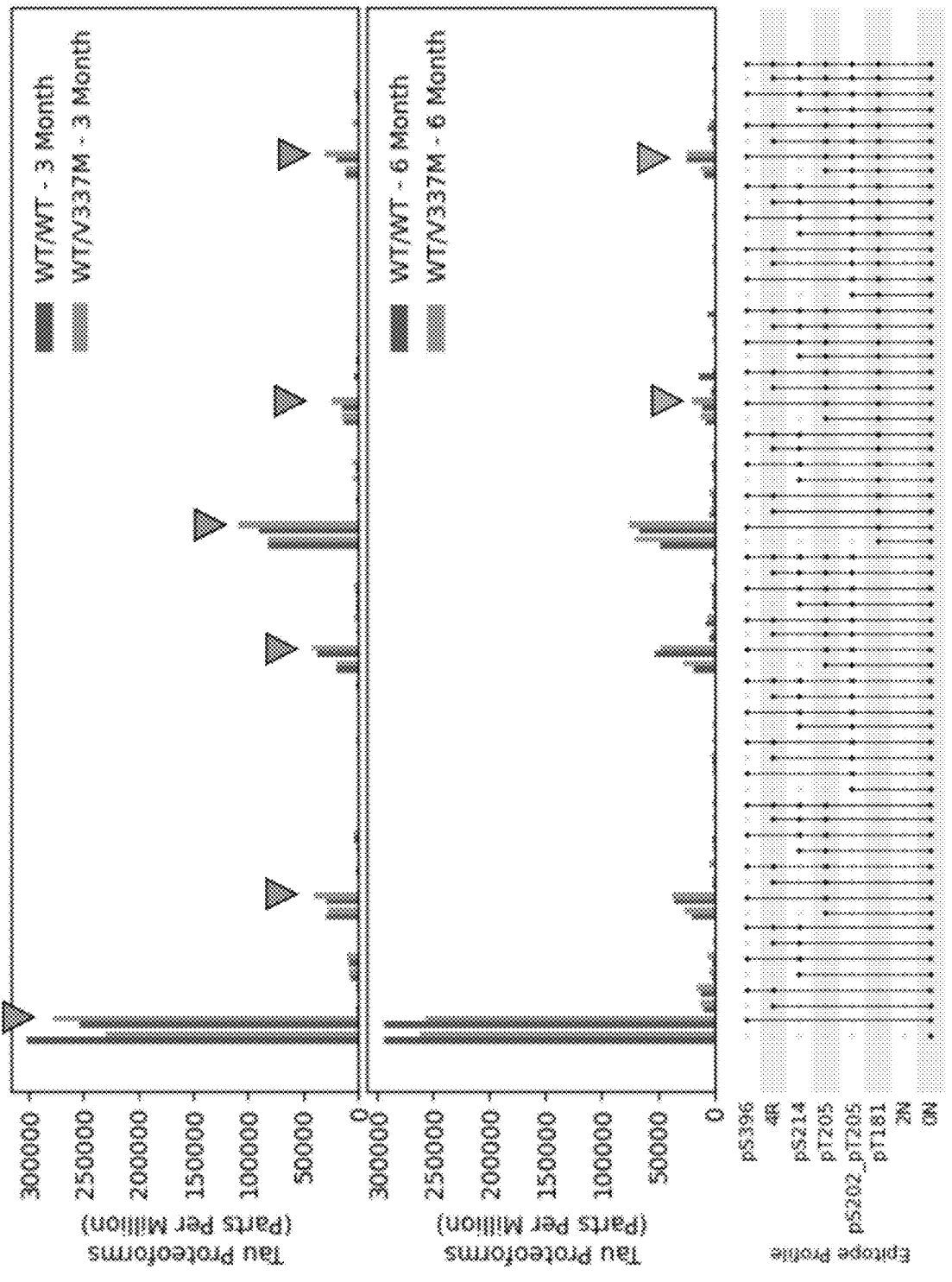
FIG. 14 shows a Tau proteoform landscape in a disease model of Frontotemporal dementia.

FIG. 14 shows a Tau proteoform landscape in a disease model of Frontotemporal dementia. Increased phosphorylation in organoids older than 3 months at S396 compared to isogenic wild-type controls has been observed. Using the techniques described herein, the most abundant 0N isoform of Tau was analyzed to identify an increase in phosphorylation of S396 over 6 months during differentiation, comparing WT with V337M mutant, confirming previous observations of S396 Tau hyperphosphorylation, as depicted in FIG. 14 with the triangles in the top chart. At single-molecule resolution, the techniques described herein also identify a rich pattern of highly phosphorylated Tau (+4 phosphorylations) within the context of intact proteins, currently impossible to observe by any other technology or techniques, as depicted with the triangles in the bottom chart of FIG. 14.

Figure 15:
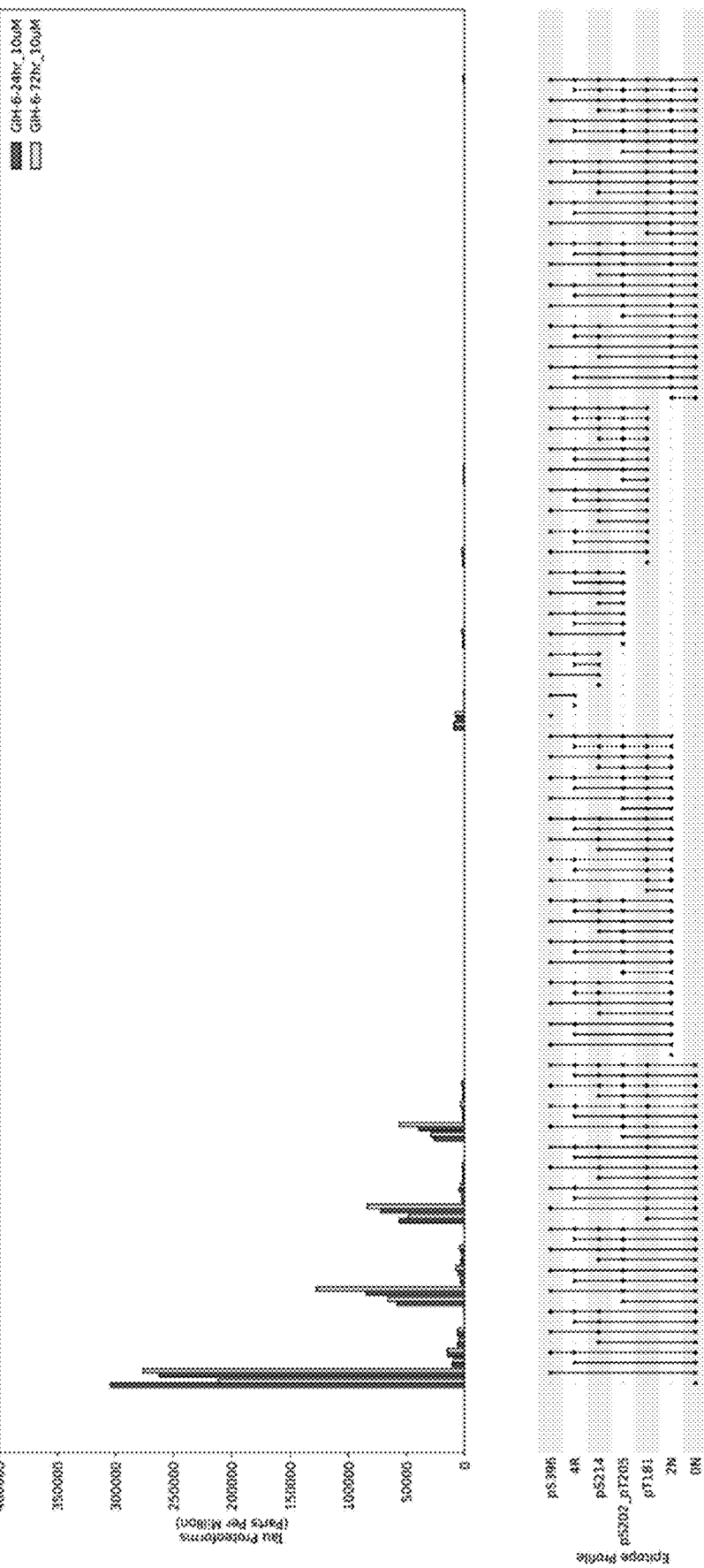
FIG. 15 shows Tau proteoforms in an organoid model system of amyloidosis.

FIG. 15 shows Tau proteoforms in an organoid model system of amyloidosis. The results depicted in FIG. 15 are obtained by applying the techniques described herein to an organoid model treated with and without amyloid beta for 24 and 72 hours. Analyzed are Tau proteoforms from WT/WT organoids using 7 site-specific antibodies (0N, 2N, 4R, pT181, pS202_pT205, pS214, pS396) with the potential to assess 128 epitope combinations. The techniques allow observation of a relative increase in unphosphorylated 0N Tau upon treatment with amyloid beta for 24 hours (dark gray bars). A concurrent decrease in the doubly phosphorylated 0N proteoforms containing pS396 (signal normalized to untreated control) is observed. Additionally, a small decrease in unphosphorylated 0N tau upon treatment with amyloid beta for 72 hours (light gray bars) and a concurrent increase in doubly phosphorylated 0N Tau is observed. A relative change in singly phosphorylated 0N-pS396 Tau at either 24 or 72 hours is not observed, highlighting the need to assess the combination of post translational modifications.

Figure 16:
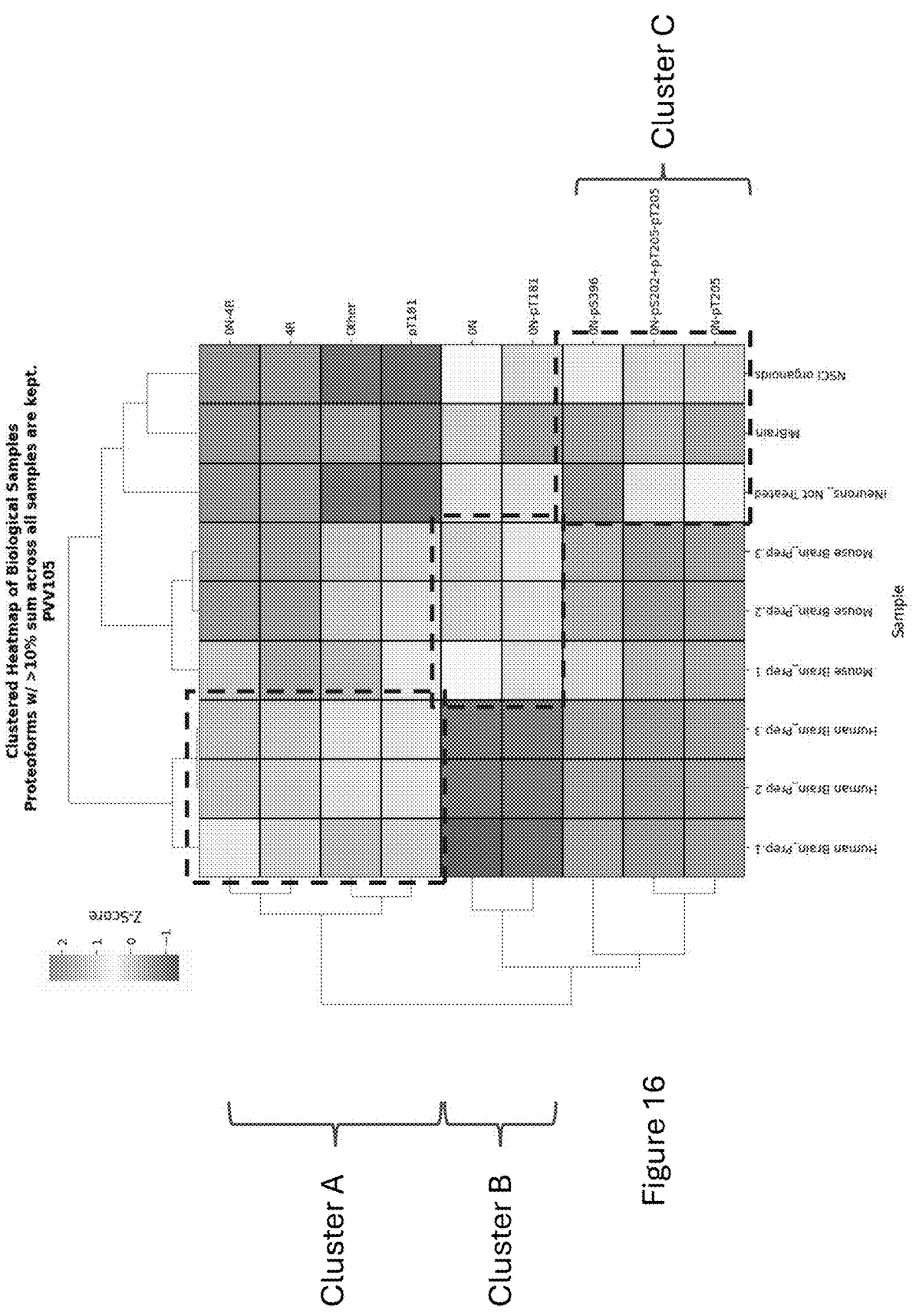
FIG. 16 shows quantification of tau proteoforms across neuronal tissue.

FIG. 16 shows quantification of tau proteoforms across neuronal tissue. The splicing of tau is regulated developmentally and only the shortest isoform (0N3R) is present in the fetal brain and maturing cellular models. This isoform may contribute to cytoskeletal plasticity during early neural development by enabling dynamic cytoskeletal adjustments needed in immature neurons. Adult tau isoforms containing 4R, on the other hand, are notably more efficient at promoting microtubule assembly. Compared were the proteoform landscapes of tau extracted from brain tissues from a cognitively normal human and a healthy mouse, as well as samples from three widely used neuronal cellular model systems; induced neurons (iNeurons), patient-derived organoids, and engineered 3D immuno-glial-neurovascular human multicellular integrated brain (miBrain) with an AD associated APOE4 gene variant. Clustering of major tau proteoforms by abundance (as shown in dashed boxes in FIG. 16) shows that each sample type has a characteristic proteoform mixture representing a particular level of tau maturation. Only data from the top 90% of proteoforms by abundance are included to improve readability.

The Human brain tau proteoform cluster contains an abundance of 4R tau isoforms with high levels of phosphorylation at pT181. NOTE: '4R' represents 1N4R and 2N4R, 'other' indicates isoforms related to 3R tau (1N3R, 2N3R). This is depicted in Cluster A in FIG. 16.

The mouse brain clusters contain an abundance Shorter 3R tau proteoforms with low levels of phosphorylation at pT181 and S396. NOTE: '0N' represents 0N3R isoforms. This is depicted in Cluster B in FIG. 16.

Cellular model system clusters contain predominantly the 0N3R form of tau with phosphorylation at several sites such as pT181, pS202, pT205 and pS396. This is depicted in Cluster C in FIG. 16.

Figure 17:
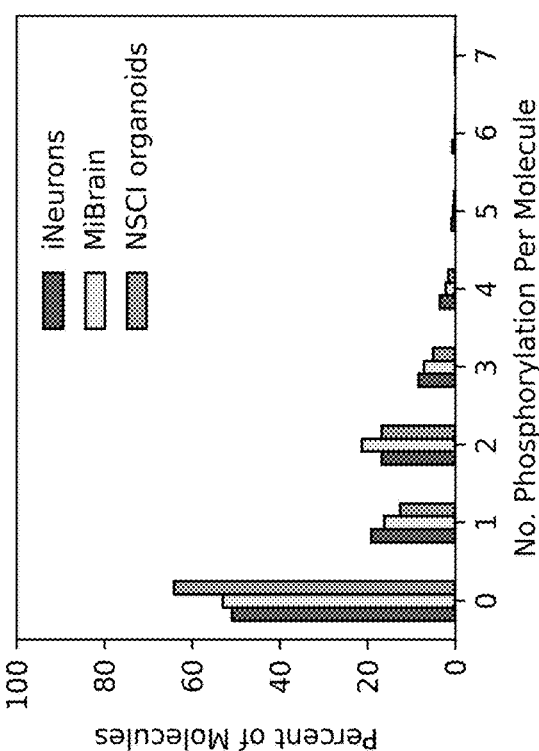
FIG. 17 shows a comparison of phosphorylation across neuronal tissue.
Figure 17:
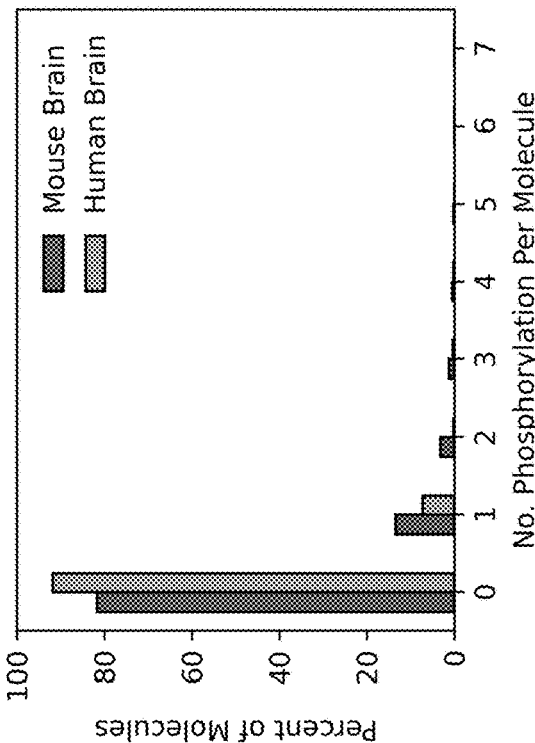

FIG. 17 shows a comparison of phosphorylation across neuronal tissue. The degree and accumulation of tau phosphorylation are closely linked to the progression of Alzheimer's disease. Higher levels of phosphorylation in tau proteins correlate with advanced stages of the disease, reflecting an increase in neurofibrillary tangles and associated cognitive decline in the human brain. In FIG. 17, the percentage of phosphorylation of human and mouse tissue is compared to neuronal cell models to illustrate an increased number of phosphorylations per tau molecule in the cell models compared to the human and mouse brain tissues. This low level of in-brain phosphorylation reflects physiological phosphorylation associated with the regulation of microtubule binding, while the higher degree of phosphorylation in the cell models is related to neuronal development in these tissues.

Figure 18:
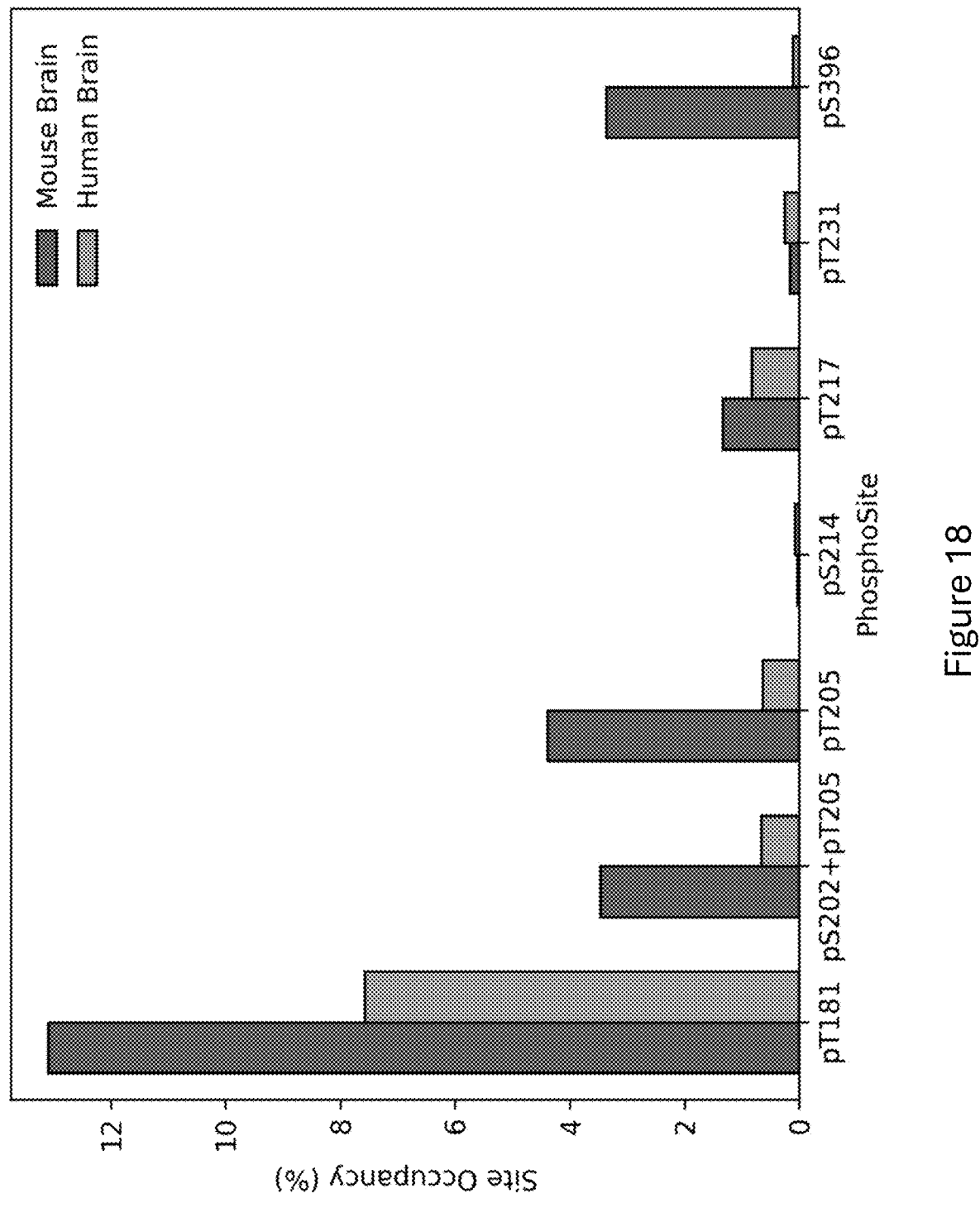
FIG. 18 shows phosphorylation across neuronal tissue.

Tau phosphorylation site occupancy in normal and disease states overlap and the qualitative location of phosphorylation sites may influence tau function in disease but is incompletely understood. As shown in FIG. 18, Human tau exhibits lower phosphorylation occupancy than mouse brain with phosphorylation at pT181 and pT231, which are involved in regulation of microtubule functions, while pS202, pT205, p S214, pT217 and pS396 are known to emerge as early markers of tau conformational changes in neurodegeneration.

Figure 19:
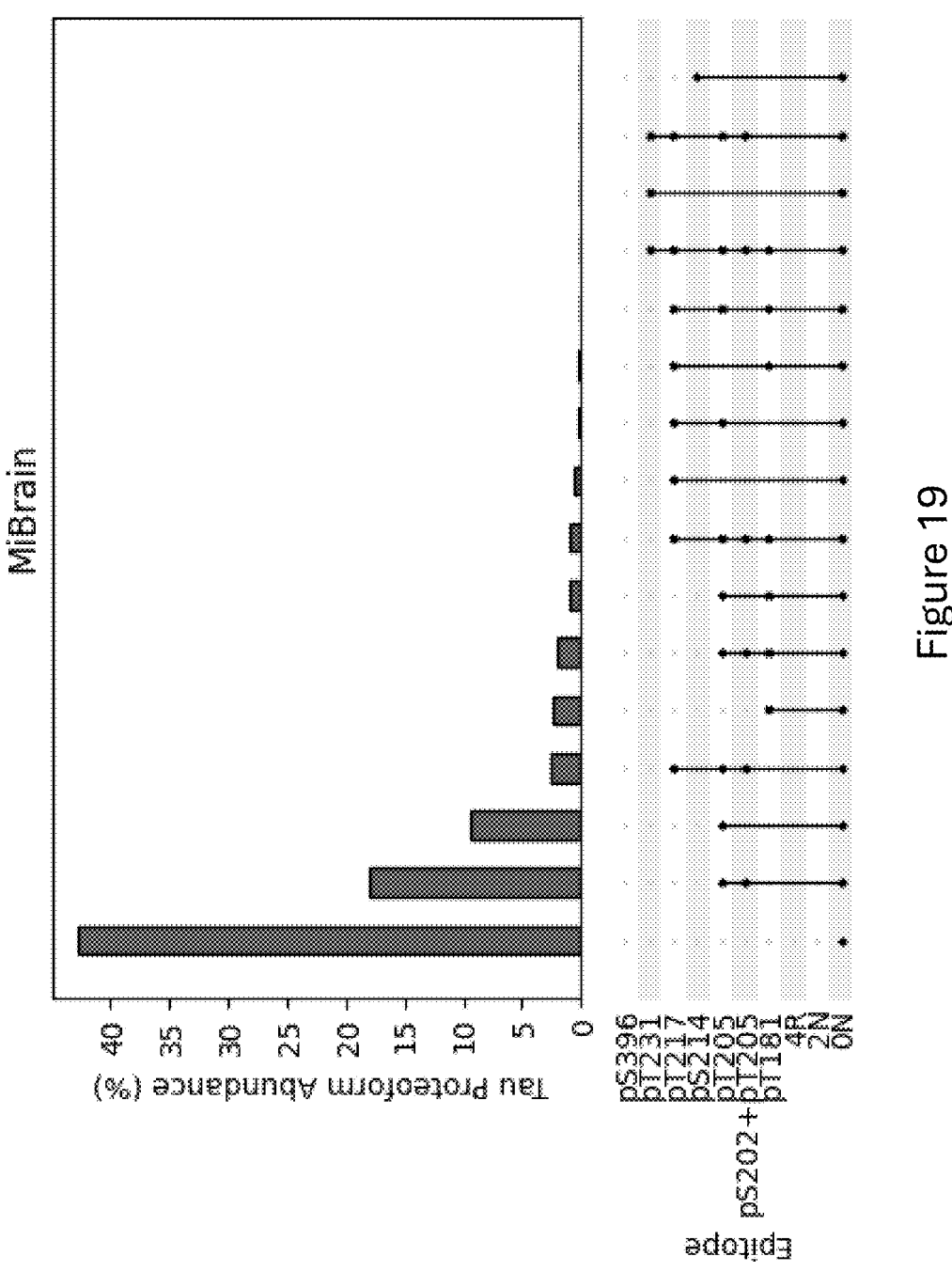
FIG. 19 shows an example of proteoform markers of tau aggregation.

FIG. 19 shows an example of proteoform markers of tau aggregation. Multisite phosphorylation is an important mechanism for regulation of tau's function and conformational changes that alter its interactions with other proteins. Early stages of abnormal tau processing have been reported to be characterized by a sequential appearance of specific phospho-dependent epitopes pT181 and pT231 followed by pS202 and pT205 cascading to pS214 and pT217 leading to tau conformational changes (See, e.g., Luna-Muoz J. et. al. J Alzheimers Dis. 2007 December; 12(4):365-75. doi: 10.3233/jad-2007-12410). In the proline-rich region of tau (aa172-aa251) pT205 is regulated by a CDK2/Cyclin A2 dependent process and the double phosphorylation at pS202+pT205 is regulated by sequential phosphorylation of CDK2/Cyclin 2A followed by GSK3beta. Single-molecule tau proteoform measurements facilitate the determination of tau proteoform abundance and the precise co-incidence of phosphorylation at one or several epitopes. Here we determine tau proteoforms in miBrains tissue with an AD associated APOE4 gene variant and find that double phosphorylation pS202+pT205 are twice as abundant as single pS202 phosphorylated tau proteoforms. Interestingly, proteoforms with four phosphorylations, e.g. pS202+pT205, pT205, pT181, p217 are detected at 4% of all tau proteoforms.

Figure 20:
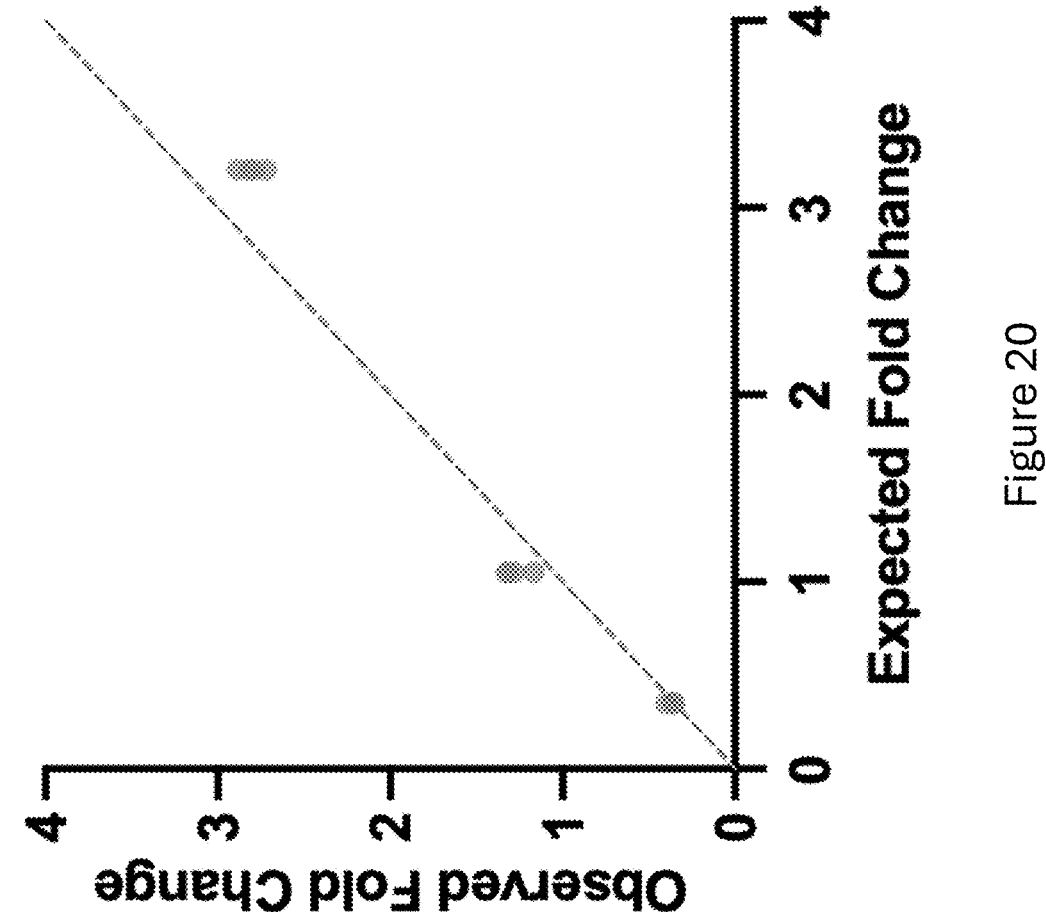
FIG. 20 shows observed fold change vs. expected fold change for tau standards in quantification assessment tests.

Mixtures of tau 2N-pS214, 2N4R and 0N4R standards with ratios of 1:2:3 or 3:2:1 were prepared and analyzed 4 times to test for reproducibility and differential quantification using a set of two pan-tau antibodies (Tau7, Tau13) probes and three epitope specific probes (0N, 2N, pS214). The detected vs. expected variations in quantification for these standards is shown in FIG. 20. Dynamic range and linearity of quantification in simple mixtures of tau standards yielded absolute abundances that were <22% different from expected, with false positives<2.5% for any given proteoform and the observed relative changes were repeatable across 4 replicates at 9-21% different from expected.

Figure 21B:
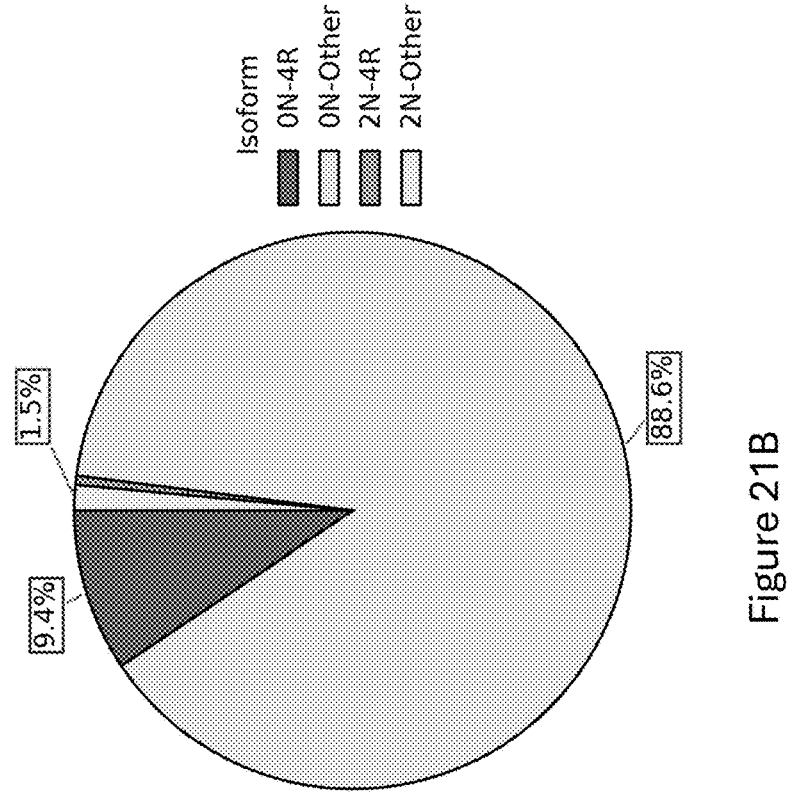
FIGS. 21A and 21B show tau isoform ontogenesis in miBrains.

The analysis methods described herein were used to assess the level of specific tau isoforms in the miBrains using seven different affinity probes (Anti-0N Anti-2N, Anti-pT181, Anti-pS214, Anti-pS396, Anti Tau13, Anti-4R). Data from one of three technical replicates is shown in FIGS. 21A and 21B.

The miBrain model integrates all six major CNS cell types which enables the miBrain to simulate the complex intercellular interactions and multicellular dynamics typical of human brain tissue, which is crucial for understanding neurodegenerative diseases.

Figure 21A:
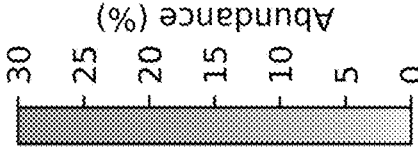
Figure 21A:
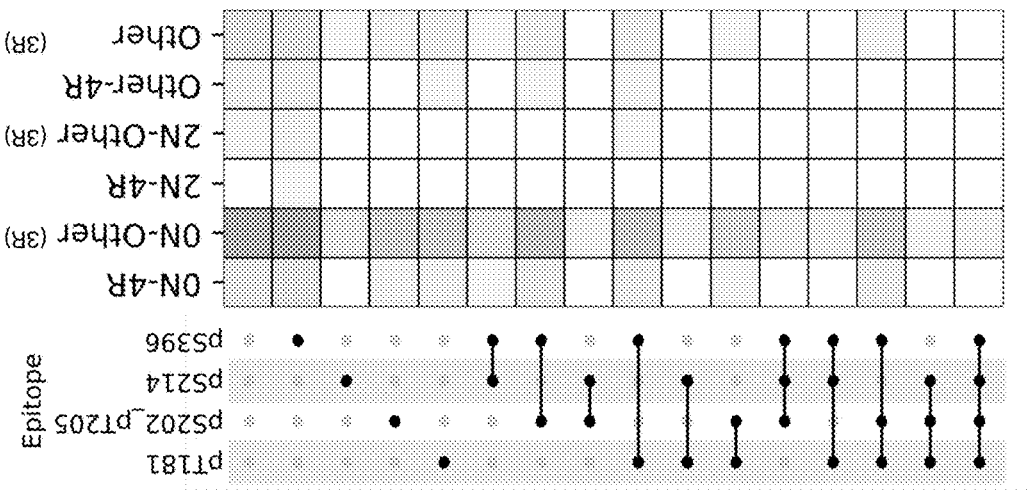

As shown in FIGS. 21A and B, the analysis identified all the 4R-tau isoforms, including the most mature and lowest abundant form of tau (2N4R) confirming the presence of tau isoforms involved in the progression of AD.

Figure 22:
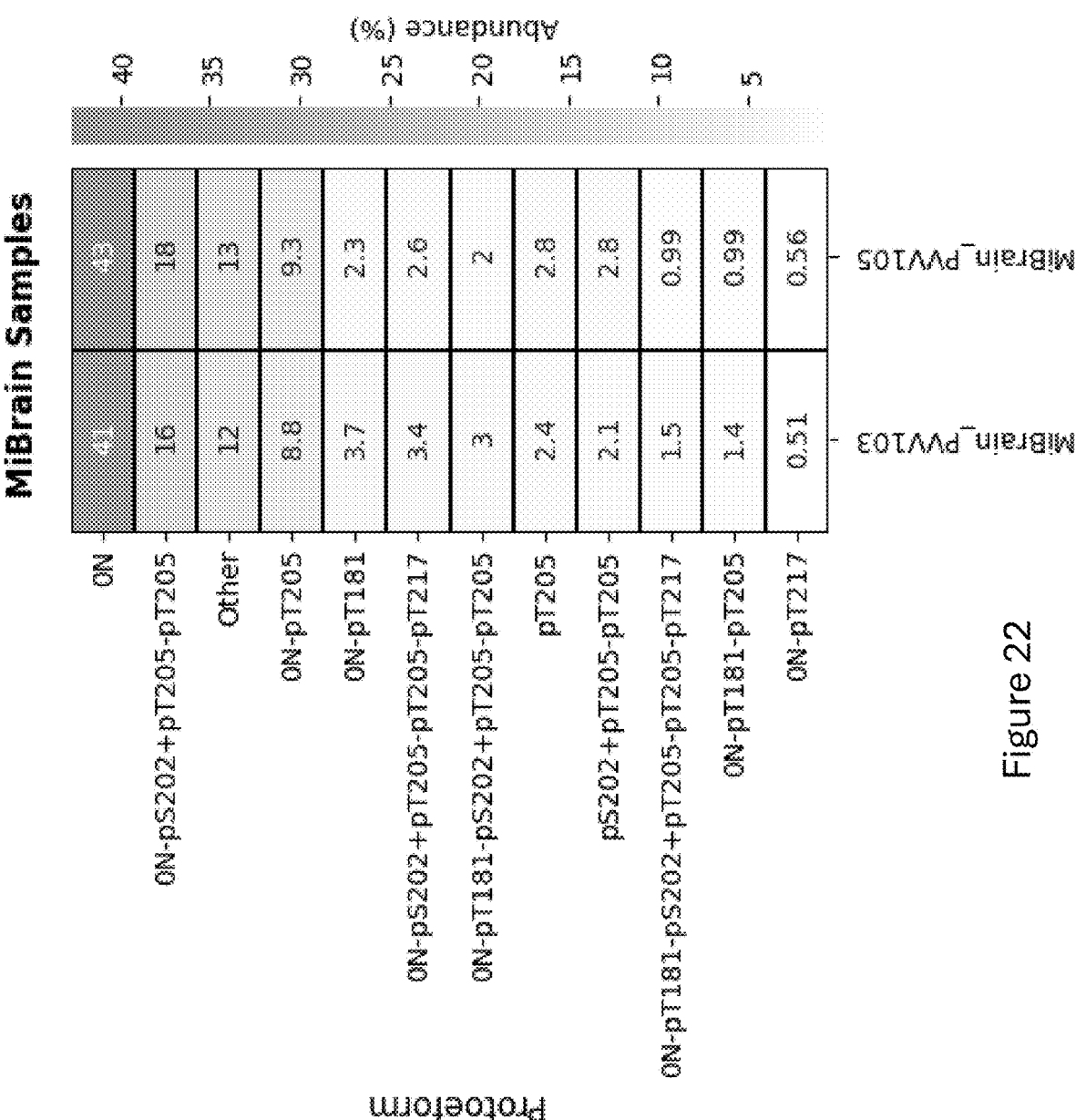
FIG. 22 shows a tau proteoform landscape in a APOE4 miBrain genotype.

FIG. 22 shows a tau proteoform landscape in a APOE4 miBrain genotype. The miBrain model has been used to study Alzheimer's disease pathologies, particularly those associated with the APOE4 genetic risk factor. The APOE4 miBrains exhibit differential behaviors such as amyloid aggregation and tau phosphorylation, which are pivotal in Alzheimer's pathology. The tau proteoform landscape in those APOE4 mi Brains is characterized using a set of 12 probes on the single-molecule proteome analysis platform.

The heatmap in FIG. 22 of the tau proteoform analysis shows the heterogeneity of tau proteoforms in APOE4 miBrains. The results also demonstrate good reproducibility between two technical replicates of the APOE4 miBrain preparation.

Figure 23:
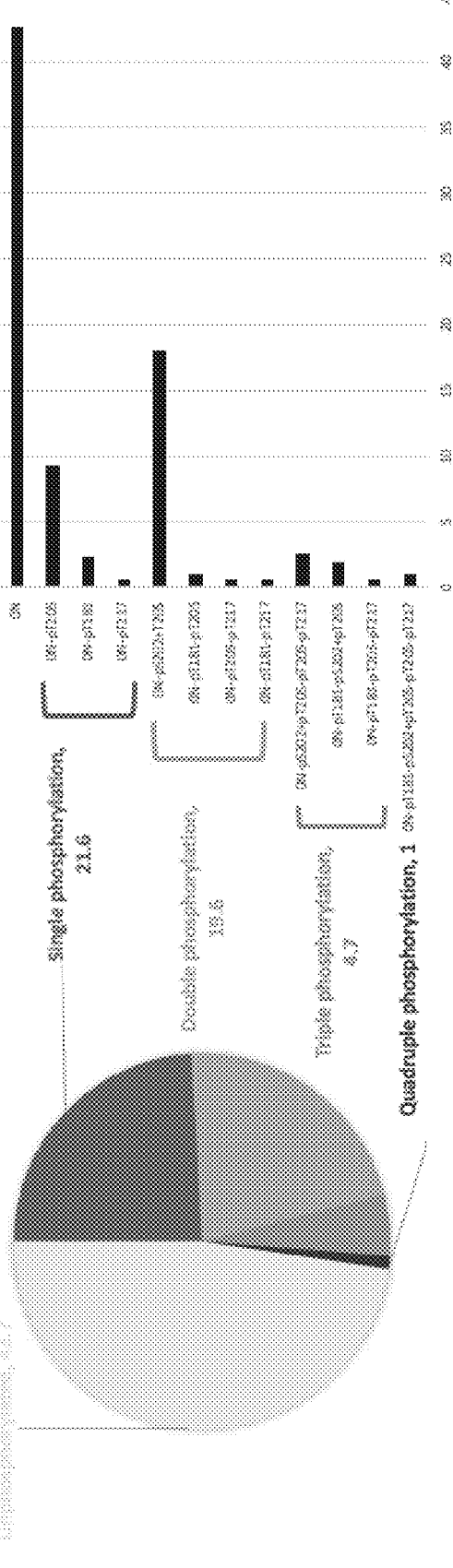
FIG. 23 shows tau proteoform phosphorylation in APOE4 miBrains.

The miBrain model allows for the incorporation of specific genetic backgrounds, such as the APOE4 gene variant, a known risk factor for Alzheimer's. Immunostaining of APOE4 miBrains indicate presence of tau phosphorylation, an AD-associated pathological marker. Tau proteins from those miBrains were extracted and subjected to tau proteoform analysis as described herein to provide a direct measure of distinct forms of phosphorylated tau exhibited in this disease model of AD, which are shown in FIG. 23. Tau is highly regulated by phosphorylation, with over 41% of all tau molecules detected with one or two (S/T) sites phosphorylated, while approximately 6% of tau molecules have three and four sites phosphorylated. pT205, which is regulated by a CDK5/Cyclin A2 dependent process has the highest phospho-site occupancy, while the double phosphorylation at pS202+pT205 (AT8 epitope), which is regulated by sequential phosphorylation of CDK5/Cyclin 2A followed by GSK3beta has the second highest phospho-site occupancy.

Notably, sites not involving pS202 or pT205 show much lower phospho-site occupancy, e.g. pT181 and pT217 and constitute only 3.2% of all tau proteoforms. In this example, Phosphorylation at sites S214, T231 and S396 was not detected or was below the detection limit.

Example 5—Characterization of Polyphosphorylated Tau Species

Data from the analysis of Tau proteoforms from model systems was then examined for evidence of interactions—where the phosphorylation status of one site potentially influences the phosphorylation of another on the same molecule. From that analysis, some phosphosite pairs were observed to have stronger interactions than others. For example, the presence of pT181 increases the probability of observing pT217 8-fold (see FIG. 23). Other phosphosites also notably increase the probability of observing pT217, including pS202+pT205 (5.2-fold), pT205 (4.3-fold), and pS214 (3.3-fold). Generally, pT217 appears to be the site most tightly coupled to the phosphorylation status of other sites on the same molecule. Conversely, pS396 appears to be the least tightly coupled to the status of the other sites on the same molecule, perhaps because it is physically further away, and outside of the proline-rich region of Tau. This is despite pS396 being the highest abundance phosphosite observed in the data. Phosphosite dependency trends appear largely conserved across model systems with some evidence of higher codependency in brain extracts. Collectively, the results highlight a complex and evolving landscape of Tau phosphoforms, where the co-occurrence of distinct phosphorylation events suggests the existence of preferential and coordinated modification pathways and the conservation of co-occurrence across model systems implies conservation of said pathways. Notably, some of these co-occurring phosphorylations span the entire length of the protein—from the N- to the C-terminus—underscoring the necessity of a methodology capable of resolving combinatorial PTM patterns across the full-length, intact tau molecule.

Figure 24:
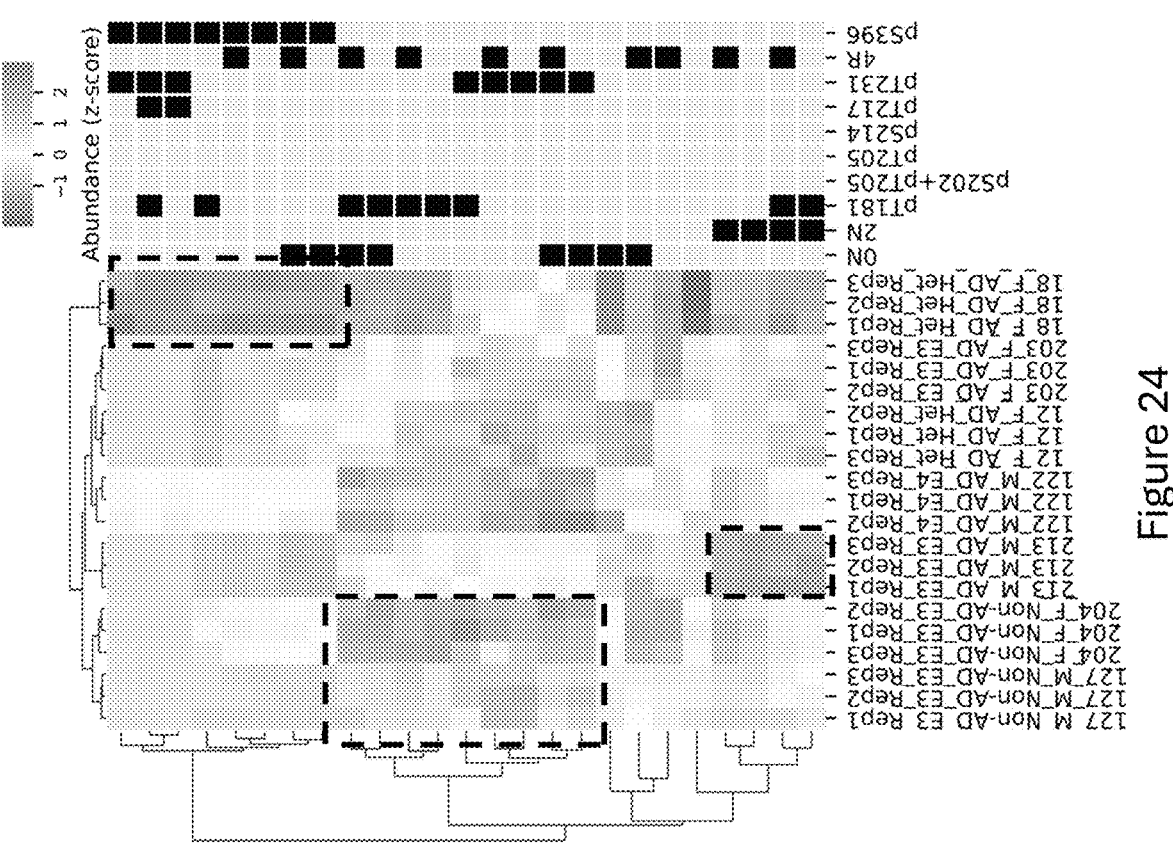
FIG. 24 shows a heat map displaying differentiated Tau proteoforms detected between brain samples from brains of Alzheimer's Disease patients and non-diseased patients.

Example 6—Characterization of Tau Protoeforms in Diverse Alzheimer Patient Populations Previous studies characterizing tau PTMs in individuals with AD have revealed considerable heterogeneity (See Wesseling et al. supra). We sought to determine whether our ability to directly measure intact tau proteoforms could enable us to distinguish between AD cases and cognitively normal controls. We measured tau proteoforms from brain samples of a small cohort of five AD patients and two Non-AD controls. Clustering of AD and non-AD samples revealed three distinct groups (shown in dashed boxes), with the Non-AD samples clustering together. Nine proteoforms differentiated the Non-AD samples from the AD samples. These nine proteoforms had abundances that were significantly different between AD and Non-AD (See FIG. 24). These proteoforms contained phosphorylation at pT181, pT231, or both sites and were found on 0N3R, 0N4R, 1N3R, and 1N4R isoforms. While this is a relatively small sample size, these results suggest that tau proteoforms from brain tissue may differentiate between AD and Non-AD.

In addition, one patient with AD exhibited higher phosphorylation than the remaining patients (Dashed box in upper right corner). This patient also exhibited the most severe pathology, as measured by ABC score (A3.B3.C3). This patient contained tau proteoforms with quadruply phosphorylated 1N3R tau at pT181-pT217-pT231-pS396. The doubly and triply phosphorylated forms of 1N3R which are a subset of the quadruply phosphorylated form suggest a regulated, rather than random, process driving these phosphorylation events. Three of four triply phosphorylated 1N3R proteoforms showed higher than expected abundance, whereas four of six doubly phosphorylated 1N3R proteoforms showed lower than expected abundance if phosphorylation events were randomly distributed. These data suggest a preference for hyperphosphorylated tau proteoforms in the patient with the most severe AD.

As illustrated above, the platform described herein is capable of characterizing and quantifying a variety of different Tau proteoforms in biological samples, including the ability to track changes in those proteoforms over time While preferred embodiments of the present invention have been shown and described herein, it will be understood to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of analyzing proteins in a first sample, comprising:

providing a population of individual protein molecules from the first sample, wherein said individual protein molecules are immobilized upon one or more solid supports and are individually addressable, and wherein the population of individual protein molecules comprises a plurality of individual molecules of a Tau protein; and identifying a plurality of proteoforms of the Tau protein in the first sample by identifying the proteoform represented by each of the plurality of individual molecules of Tau protein on the one or more solid supports based upon identification of a presence or absence of at least 3 different modifications within each of the individual molecules of the Tau protein.

2. The method of claim 1, wherein the identifying step comprises identifying a presence or absence of at least 5 different modifications to each of the individual molecules of the Tau protein.

3. The method of claim 2, wherein at least 3 of the at least 5 different modifications of Tau protein are selected from the group of pT181, pS202, pT205, pS214, pT217, and pT231.

4. The method of claim 2, wherein at least 2 of the at least 5 different modifications of Tau protein are selected from the group of ON, IN, 2N, 3R and 4R isoforms of Tau protein.

5. The method of claim 1, wherein the providing step comprises enriching for the individual molecules of the Tau protein from the first sample prior to immobilizing the individual molecules of the Tau protein onto the one or more solid supports.

6. The method of claim 5, wherein the enriching step comprises:

contacting the individual molecules of Tau protein in the first sample with beads coated with antibodies that specifically bind to Tau proteins under conditions to promote binding of the antibodies to the individual molecules of Tau protein in the first sample;

washing the beads to remove unbound material;

contacting the beads with a polypeptide that mimics or duplicates a portion of Tau protein that is bound by the antibodies under conditions whereby the polypeptide competes with the Tau protein for binding to the antibodies, thereby releasing the individual molecules of Tau protein from the antibodies; and collecting enriched Tau protein.

7. The method of claim 5, comprising spiking in a known amount of a standard protein into the first sample prior to the enriching step.

8. The method of claim 1, wherein the identifying step comprises identifying a presence or absence of at least 7 different modifications to each of the individual molecules of the Tau protein.

9. The method of claim 1, wherein the identifying step comprises identifying a presence or absence of at least 10 different modifications to each of the individual molecules of the Tau protein.

10. The method of claim 1, wherein the one or more solid supports comprises an array surface, and the population of individual protein molecules are immobilized on individually addressable locations of the array surface.

11. The method of claim 10, wherein the individual protein molecules are individually coupled to separate structured nucleic acid particles which are immobilized on the array surface.

12. The method of claim 1, wherein the first sample comprises at least 5 different proteoforms of the Tau protein.

13. The method of claim 12, wherein the first sample comprises at least 20 different proteoforms of the Tau protein.

14. The method of claim 1, wherein the identifying step is configured to identify at least 5 different proteoforms of the Tau protein.

15. The method of claim 14, wherein the identifying step is configured to identify at least 20 different proteoforms of the Tau protein.

16. The method of claim 15, wherein the identifying step is configured to identify at least 100 different proteoforms of the Tau protein.

17. The method of claim 1, further comprising the step of quantifying an amount of each of the plurality of different proteoforms of the Tau protein in the first sample identified in the identifying step.

18. The method of claim 1, wherein identifying the presence or absence of modifications within each individual molecule of the Tau protein comprises:

contacting the individual molecules of the Tau protein with a plurality of affinity reagents, wherein each of the plurality of affinity reagents comprises a specific binding affinity for a different modification to the Tau protein; and detecting whether each of the plurality of affinity reagents binds to individual molecules of the Tau protein.

19. The method of claim 1, further comprising repeating the providing and identifying steps with a population of individual protein molecules from a second sample that comprises a plurality of molecules of the Tau protein, and comparing proteoforms of the Tau protein identified from the first sample to proteoforms of the Tau protein identified from the second sample.

20. The method of claim 19, wherein the providing and identifying steps are repeated with a population of individual protein molecules from at least 10 different samples.

21. The method of claim 20, wherein the providing and identifying steps are repeated with a population of individual protein molecules from at least 100 different samples.

22. The method of claim 21, wherein the providing and identifying steps are repeated with a population of individual protein molecules from at least 1000 different samples.

23. The method of claim 1, wherein the population of individual protein molecules comprises a plurality of individual protein molecules of a second protein of interest, and the identifying step further comprises identifying proteoforms of the second protein of interest.

* * * * *